(12) United States Patent
Jayakumar et al.

(10) Patent No.: US 8,012,752 B2
(45) Date of Patent: Sep. 6, 2011

(54) IN VITRO METHODS FOR THE INDUCTION AND MAINTENANCE OF PLANT CELL LINES AS SINGLE SUSPENSION CELLS WITH INTACT CELL WALLS, AND TRANSFORMATION THEREOF

(75) Inventors: P. Samuel Jayakumar, Carmel, IN (US); Jeffrey Beringer, Carmel, IN (US); Paul R. Schmitzer, Indianapolis, IN (US); Frank Burroughs, Noblesville, IN (US); Robbi J. Garrison, Filmore, IN (US); William M. Ainley, Carmel, IN (US); Narasimha C. Samboju, Carmeil, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 778 days.

(21) Appl. No.: 11/965,543

(22) Filed: Dec. 27, 2007

(65) Prior Publication Data

US 2010/0159598 A1 Jun. 24, 2010

Related U.S. Application Data

(60) Provisional application No. 60/878,028, filed on Dec. 29, 2006.

(51) Int. Cl.
*C12N 5/00* (2006.01)
*C12N 5/02* (2006.01)

(52) U.S. Cl. .......................... 435/420; 435/410; 435/431

(58) Field of Classification Search .................. 435/420, 435/410, 431
See application file for complete search history.

(56) References Cited

OTHER PUBLICATIONS

Umetsu et al. Enhancement of Cell Separation by Colchicine in Cell Suspension Cultures of Soybean, Planta (Berl.),125, pp. 197-200, 1975.*
Nagata et al. "Cell Wall Regeneration and Cell Division in Isolated Tobacco Mesophyll Protoplasts," Planta (Berl.) 92, pp. 301-308, (1970).*
Hayashi et al. "Cell expansion and single-cell separation induced by colchicine in suspension-cultured soybean cells," Proc. Natl. Acad. Sci. USA vol. 85, pp. 2618-26-22, Apr. 1988, Cell Biology.*
Vu et al. "Glycerol stimulation of chlorophyll synthesis, embryogenesis, and carboxylation and sucrose metabolism enzymes in nucellar callus of 'Hamlin' sweet orange," Plant Cell, Tissue and Organ Culture 33: 75-80, 1993.*

Hayashi, T., Cell Expansion and Single-Cell Separation Induced by Colchicine in Suspension-Cultured Soybean Cells, National Academy of Sciences of the United States of America, vol. 85, No. 8, 1988, pp. 2618-2622, whole document.
Matsumoto, S., Charachterization of a Human Glycoprotein (Erthropoietin) Produced in Cultured Tobacco Cells, Plant Molecular Biology, Springer, Dordrecht, NL,, vol. 27, No. 6, Mar. 1, 1996, pp. 1163-1172, whole document.
Umetsu, N., Enhancement of Cell Separation by Colchicine in Cell Suspension Cultures of Soybean, Planta, Springer Verlag, DE, vol. 125, No. 2, 1975, pp. 197-200, whole document.
Naill, M., Culture of Isolated Single Cells from Taxus Suspensions for the Propagation of Superior Cell Populations, Biotechnology Letters, Kluwer academic Publishers, DO, vol. 27, No. 21, Nov. 1, 2005, pp. 1725-1730, whole document.
Lee, T., Establishment of Rapidly Proliferating Rice Cell Suspension Culture and Its Characterization by Flourescence-Activated Cell Sorting Analysis, Plant Molecular Biology Reporter, vol. 22, No. 3, Sep. 2004, pp. 259-267, whole document.
Sabri, N., Transient and Stable Electrotransformations of Intact Black Mexican Sweet Maize Cells are Obtained after Preplasmolysis, Plant Cell reports, Springer Verlag, DE, vol. 15, No. 12, Jan. 1, 1996, pp. 924-928, whole document.
Keates, R., Stabilization of Microtubule Protein in Glycerol Solutions, Canadian Journal of Biochemistry, vol. 59, No. 5, May 1, 1981, pp. 353-360, XP008094832, ISSN: 0008-4018, p. 353.
Morejohn, L., Inhibition of Plant Microtubule Polymerization In Vitro by Phosphoric Amide Herbicide Amiprophos-methyl, Science 1984 US, vol. 224, No. 4651, 1984, pp. 874-876, whole document.
Smith, M., Disphenyl Pyrazole Herbicides, Abstracts of Papers American Chemical Society, vol. 221, No. 1-2, 2001, p. AGRO 6, XP008094856 & 221st National Meeting of the American Chemical Society, San Diego, CA, USA, Apr. 1-5, 2001, ISSN: 0065-7727, abstract.

* cited by examiner

*Primary Examiner* — Susan McCormick Ewoldt
(74) *Attorney, Agent, or Firm* — Ronald S. Maciak; Baker & Daniels LLP

(57) ABSTRACT

The subject invention provides simple and consistent methods to break suspension cell aggregates to single cells with intact primary cell walls. The subject invention relates in part to cell separation of suspension cell aggregates cultured in medium containing pectin-degrading enzymes or tubulin depolymerizing compounds including colchicine. The subject invention also relates to novel uses of compounds for such purposes. Another aspect of the subject invention relates to transformation of the subject, isolated cells. Such processes simplify and integrate single-cell-based transformation and selection processes into transgenic and transplastomic event-generation work processes. The subject invention also removes technical constraints and produces marker-free and uniformly expressing transgenic lines in a high throughput fashion to support various needs of animal health, biopharma, and trait and crop protection platforms.

3 Claims, 10 Drawing Sheets
(8 of 10 Drawing Sheet(s) Filed in Color)

Add MT disruptors (25 nM to 1 mM) to the medium soon after suspension initiation
↓
Release single cells 3-7 days after suspension initiation
↓
Obtain high percentage of single cells after 7 days of treatment
↓
Strain single cells through 100, 75, and 40 uM filters to remove any dead cell aggregates
↓
Plate 1.5 ml single cells at 0.6 OD$^{600}$ density on a LS BY2 plate with 10 mg/L Bialophos for 2-4 weeks to pick colonies

FIG. 7

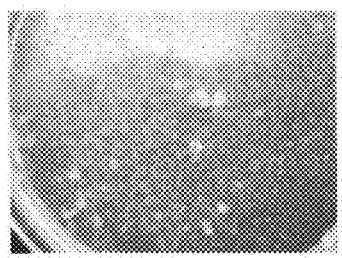 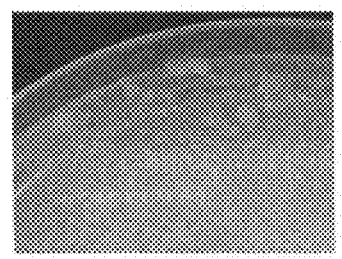 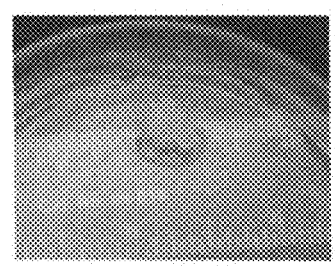

FIG. 8A    FIG. 8B    FIG. 8C

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<221> NAME/KEY: Primer for MAS394

<400> SEQUENCE: 1
tatgctgcgt tcgggaagga tgaa                                            24

<210> SEQ ID NO 2
<211> LENGTH: 24
<212> TYPE: DNA
<213> ORGANISM: Artificial Sequence
<220> FEATURE:
<221> NAME/KEY: Primer for MAS395

<400> SEQUENCE: 2
gattaaaaga ataaacatcc gatg                                            24

<210> SEQ ID NO 3
<211> LENGTH: 24
<212> TYPE: DNA
<213> ORGANISM: Artificial Sequence
<220> FEATURE:
<221> NAME/KEY: Primer for MAS396

<400> SEQUENCE: 3
ttgcctaaga gaggatgcat cgga                                            24
```

<210> SEQ ID NO 4
<211> LENGTH: 24
<212> TYPE: DNA
<213> ORGANISM: Artificial Sequence
<220> FEATURE:
<221> NAME/KEY: Primer for MAS397

<400> SEQUENCE: 4
ttgtctgttg tgcccagtca tagc                                    24

<210> SEQ ID NO 5
<211> LENGTH: 24
<212> TYPE: DNA
<213> ORGANISM: Artificial Sequence
<220> FEATURE:
<221> NAME/KEY: Primer MAS398

<400> SEQUENCE: 5
tgatattgct gaagagcttg gcgg                                    24

<210> SEQ ID NO 6
<211> LENGTH: 24
<212> TYPE: DNA
<213> ORGANISM: Artificial Sequence
<220> FEATURE:
<221> NAME/KEY: Primer MAS399

<400> SEQUENCE: 6
ttggtgtagc cgccgttgtt gatg                                    24

<210> SEQ ID NO 7
<211> LENGTH: 24
<212> TYPE: DNA
<213> ORGANISM: Artificial Sequence
<220> FEATURE:
<221> NAME/KEY: Primer MAS400

<400> SEQUENCE: 7
tggagtacca gcacgccttc aagc                                    24

<210> SEQ ID NO 8
<211> LENGTH: 24
<212> TYPE: DNA
<213> ORGANISM: Artificial Sequence
<220> FEATURE:
<221> NAME/KEY: Primer MAS401

<400> SEQUENCE: 8
ggctatgcca tcctaaggtg ctgc                                    24

IN VITRO METHODS FOR THE INDUCTION AND MAINTENANCE OF PLANT CELL LINES AS SINGLE SUSPENSION CELLS WITH INTACT CELL WALLS, AND TRANSFORMATION THEREOF

CROSS-REFERENCE TO RELATED APPLICATION

This application claims the benefit of provisional application Ser. No. 60/878,028, filed Dec. 29, 2006.

FIELD OF THE INVENTION

The invention pertains in part to the field of propagation of plant cell lines, including methods of propagating plant cells in suspensions as single cells.

BACKGROUND OF THE INVENTION

Over the past two decades, there has been a rapid emergence of plant genetic engineering technology coupled with major improvements in the development of large-scale plant cell culture processes for the production of useful secondary metabolites. From 1995 (Moffat, 1995; Ma et al., 2003), such plant cell suspension cultures are increasingly used as a valuable host cell system for the expression of recombinant proteins.

Auxin-induced callus tissue or suspensions, in spite of their single tissue origin, usually contains cells with a variety of phenotypes. Thus, transgenic lines developed from such cell types are usually highly heterogeneous with inconsistent expression levels. Therefore, clones producing many useful secondary metabolites have been obtained from single protoplasts, i.e., a high shikonin-producing cell clone prepared from *Lithospermum erythrorhizon* protoplasts (Maeda et al., 1983).

So far, it has been necessary to form protoplasts to disaggregate cells not only for cell selection but also for electroporation/PEG mediated transformation of cultured plant cells. Protoplast preparation has been required for the isolation of single cell clones from plant tissues. However, it is usually difficult for protoplasts to regenerate their normal walls, because isolated protoplasts are usually arrested and reluctant to divide (Hahne and Hoffmann, 1984). In many studies on cultured protoplasts, the first and major polysaccharide generated is callose, which is composed of 1,3-, 8-glucopyranoses (Klein et al., 1981).

Wounded or stressed plants often secrete masses of this glucan into periplasmic spaces (Currier, 1957). During early stages of wall regeneration, binding between cellulose and xyloglucan is not as strong as it is in intact plants (Hayashi et al., 1986). Since the macromolecular organization of xyloglucan and cellulose in the primary cell walls appears to be responsible for the strength and extensibility (Hayashi and Maclachlan, 1984), the deposition of xyloglucan as well as cellulose around protoplasts appears to be critical to their division and growth potential. This prerequisite stalls the division of protoplast, thus increasing the time to regenerate into normal cells with the cellular characteristics of the parental lines.

An ongoing technical challenge, therefore, in the field of plant cell culture is to isolate single viable cells that can be cloned from plant tissue in culture (Bourgin, 1983; Tabata et al., 1976). In suspension culture, non-uniform cell aggregates always form, and each such aggregates contain up to hundred cells. Nothing is known about the linkage between these aggregated cells, and there has been no report identifying a single enzyme that can dissociate cell aggregates and maintain them as single cells in vitro with intact cell walls.

Pectin's role in cell adhesive properties was suggested in several reports, but such a link was established relatively more recently (Bouton et al., 2002). In addition, strong reductions in cell adhesive properties were reported (Sterling et al., 2006).

The qual-1 mutants showed detached single root cells (Bouton et al., 2002). The reduced pectin content was corroborated further by immunofluorescence experiments using antibodies raised against specific pectic epitopes. These observations suggest that the encoded enzyme may be involved in the synthesis of pectic polysaccharides and clearly indicated pectin is involved in the adhesive properties of plant cells.

Thus, disrupting pectin synthesis to remove cell adhesive properties can facilitate cell separation. Single cell isolation with one time pectin degrading enzyme treatments (Naill, 2005) has been reported to aid isolation of single cells in Taxus cell suspension cultures. Such Taxus single cells are used to screen for elite clonal lines with higher level of Taxol production. However, this method is not useful in the maintenance of single suspension cells in the continuous presence of the enzyme in the medium. Also, the highest single cell yield with such short pulse treatment of enzymes or combination of enzymes was only 17.1% to 34.4% (Naill, 2005). Continuous pectinase treatment in rice suspensions have only resulted in fine suspension aggregates at 0.005% concentrations but has not helped to maintain the suspension as single cells (Lee et al., 2004). Prolonged treatments of combination of enzymes, pectinase and cellulase for more than 8 hours have resulted in cell lysis (Naill, 2005).

Enhancement of cell separation in suspension cultures of soybean cells has been reported to be enhanced in the presence of colchicine (Umetsu et al., 1975). For cell separation the alkaloid was added to culture medium at lower concentrations (0.1-1.0 mM) than those (5-20 mM) for the production of chromosomal polyploidy. Nonetheless, colchicine inhibits mitosis in plant and animal cells (Lewin, 1980). Colchicine binds to tubulin and prevents the assembly of microtubules. Therefore, to obtain cell separation, the colchicines concentration and treatment time should be as low as possible.

Colchicine alkaloids have been used for synchronization of growth in cultured animal cells where the alkaloids are usually added at 0.5 mM, and the cells should be arrested within a few hours, before the mitosis. Although the morphogenic effect is quite similar to that in animal cells, plant cells can divide during growth in the presence of colchicine at 0.1 mM (Umetsu et al., 1975). Cell viability decreased after 4 days of culture of soybean suspension cells in 1 mM colchicine. In addition, only 44.8% of the cells were viable in these treatments, but it was possible to keep them dividing unlike in animal cells.

The use of tubulin depolimerization inhibitors or on the oligosaccharins in the maintenance of single cell suspension in plant in vitro cultures has been investigated. The literature has some information as early as 1975 regarding using colchicines for cell separation; see References section, below. Tubulin inhibitors as herbicides have also been investigated.

Elite transgenic event production and recovery relies heavily on the development of enabling technologies. Current methods in place for transformation of suspension cell aggregates is *Agrobacterium*- and whisker-mediated methods. *Agrobacterium* method shows a backbone integration rate of up to 67-90% making it a very inefficient process, where WHISKERS™ mediated transformation will not serve as a high throughput process (HTP). The PEG mediated method is used always demonstrated with protoplast and the protoplast of tobacco though easy to transform, it is not amenable easily for HTP transformation process due to the problems of cell wall regeneration.

The art appears to be silent regarding protocols for single-cell-suspension-culture-based transformation. There are several reports on protoplast-based protocols, but these are devoid of cell walls unlike single cell suspensions of plant cells as discussed below.

BRIEF SUMMARY

The subject invention provides simple and consistent methods to break suspension cell aggregates to single cells with intact primary cell walls. The following disclosure discusses cell separation of suspension cell aggregates cultured in medium containing pectin-degrading enzymes or tubulin de-polymerizing compounds including colchicine.

The subject invention also relates to novel uses of compounds for such purposes.

One aspect of the subject invention relates to transformation of the subject, isolated cells. Such processes simplify and integrate single-cell-based transformation and selection processes into transgenic and transplastomic event-generation work processes. The subject invention also removes technical constraints and produces marker-free and uniformly expressing transgenic lines in a high throughput fashion to support various needs of animal health, biopharma, and trait and crop protection platforms.

BRIEF DESCRIPTION OF THE FIGURES

The patent or application file contains at least one drawing executed in color. Copies of this patent or patent or patent application publication with color drawing(s) will be provided by the Office upon request and payment of the necessary fee.

A—Normal BY2 suspension; B—Same as A, but I2KI stained cells to show the aggregation of cells; C and D—Separated cells after 6 days of continuous enzyme treatment; E and F—Separated single cells with and without I2KI staining. Note the normal cell division (F)

Figure 2:
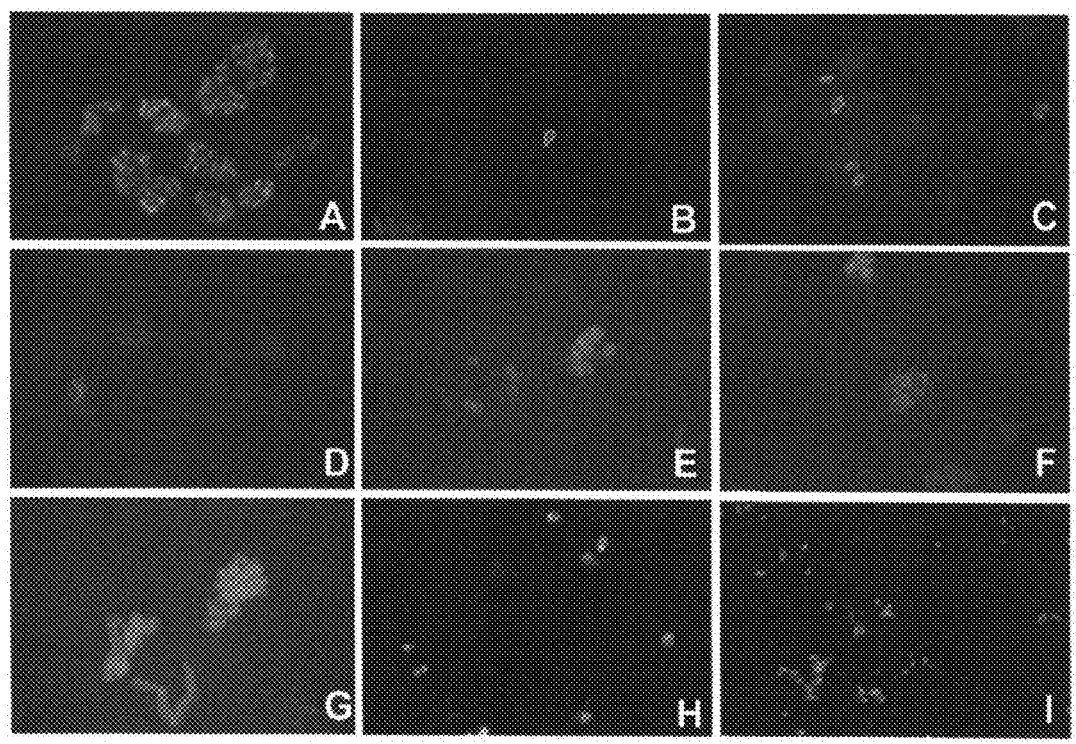

FIG. 2: Viability of the BY2 cells 6 days after continuous Pectolyase treatment (cells are treated with FDA and PI) and the yield of single cells.

A: BY2 cell aggregates; B: BY2 in 1 ml inoculum in Pectolyase in the medium for 5 days; C: 6 ml inoculum with enzyme in the medium day 5; D, E, and F: Microscope field snap shots of C; G: control clumps with BY2 cell variant developed in BAP and 12% sucrose; H and I single cells from 5 days of continuous enzyme treatment from G. Cells stained in FDA and PI. Note the dead cells in PI stained red.

Figure 3:
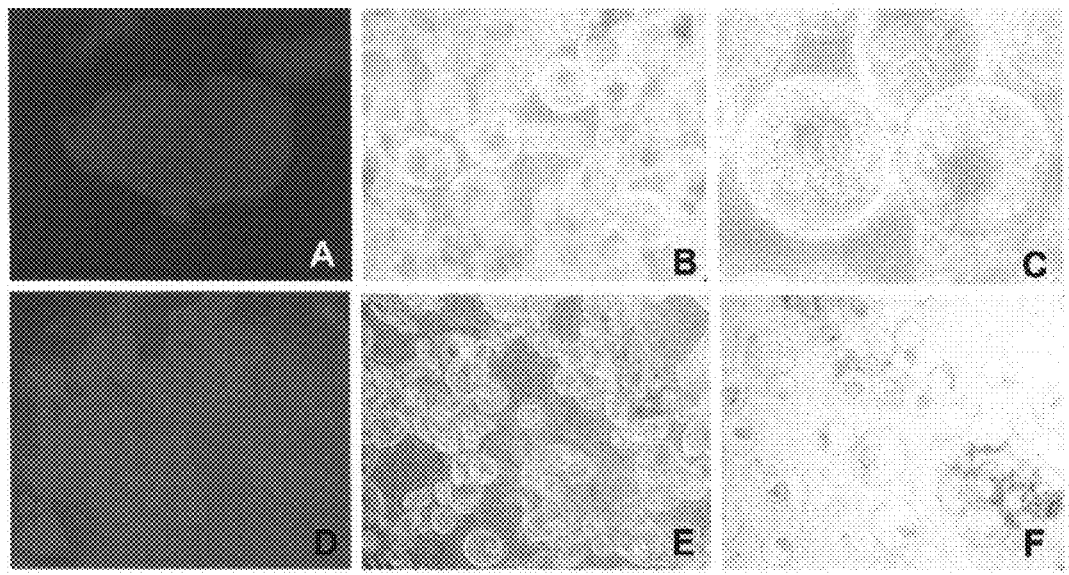

FIG. 3: Single cell suspension induction from 7 day Colchicine treatments in the medium from the cell aggregate suspensions of BY2 and Xanthi tobacco suspension.

A: Normal BY2 suspension aggregate (Calcafluor stained); B: Single Cell BY2 suspension in 1 mM Colchicine for 7 days; C: Same as B, but enlarged to show single cells with intact walls; D: Suspension aggregates of Xanthi; E: Xanthi suspension aggregates treated for 7 days in 0.5 mM Colchicine. Note the partial release of single cells in 0.5 mM; and F: Separated single cells of Xanthi in 1 mM Colchicine.

Figure 4:
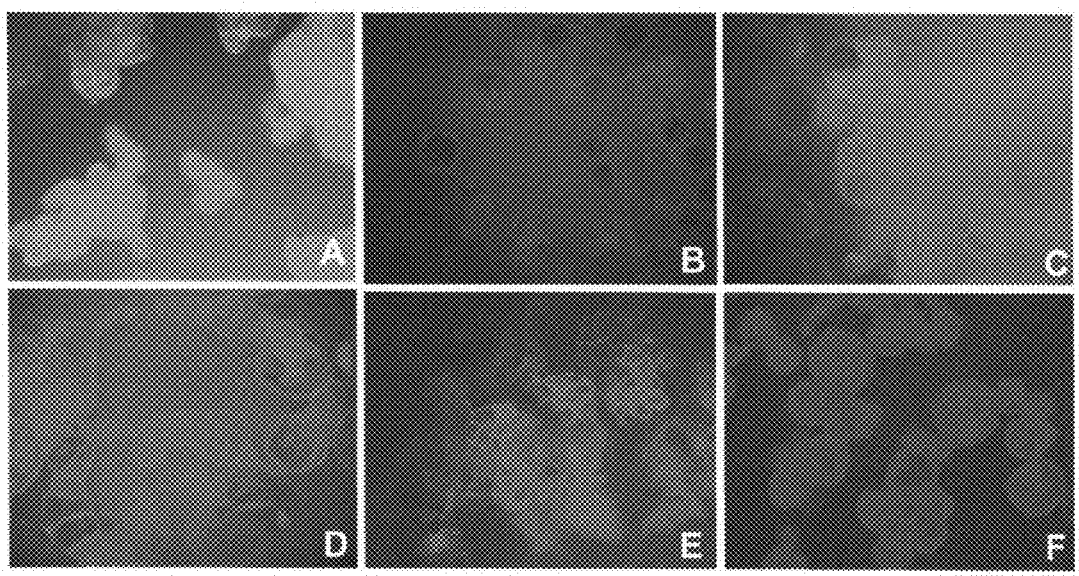

FIG. 4: Single cell release with intact cell walls in Colchicine treatments from BY2- and Xanthi tobacco suspension aggregates.

A: Normal BY2 suspension aggregates B: Single Cell BY2 suspension in 1 mM Colchicine for 7 days; C and D: Recovery of cells back to aggregates after removal of Colchicine (4d after subculture with 1 culture cycle of colchicine treatment); E: Suspension aggregates of Xanthi; F: Xanthi suspension aggregates treated for 7 days in 1 mM Colchicine. Note the released single cells in BY2 and Xanthi cultures and the presence of the intact cell wall as seen in the presence of the optical brightener, Calcafluor. (All samples treated with 0.1% of Calcafluor and examined under Leica fluorescent scope).

Figure 5:
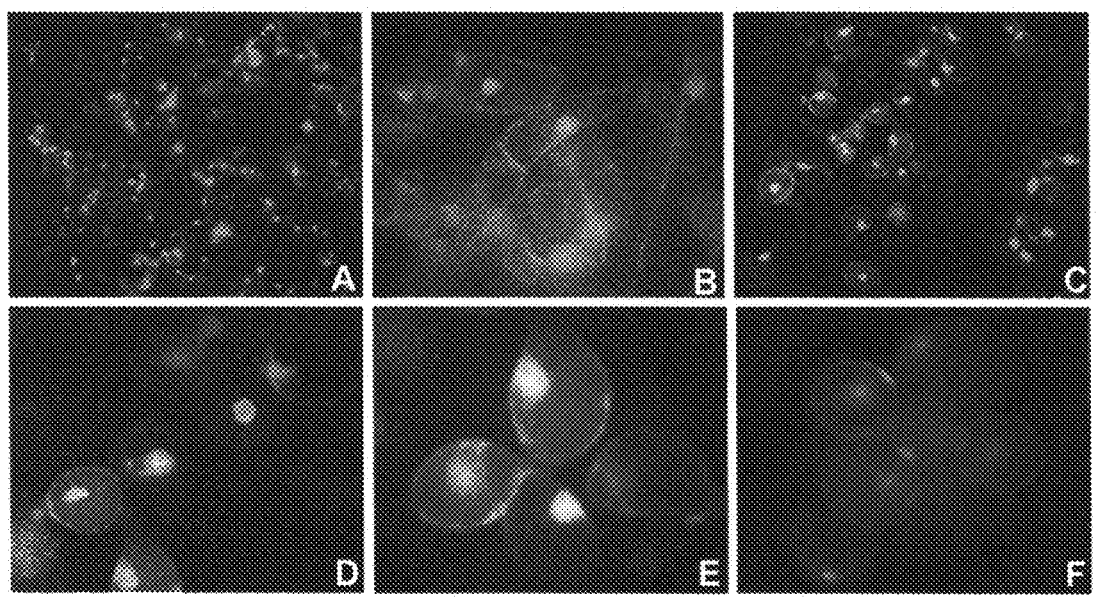

FIG. 5: Single viable cell release with intact cell walls in Colchicine treatments from BY2-Variant tobacco (habituated in EP 12% sucrose medium) and Jimson weed suspension aggregates.

A: Normal BY2-V suspension aggregates B: Closer view of the untreated aggregates; C, D and E: Single Cell BY2 suspension induction in 1 mM Colchicine for 7 days (Cells under 10×, 20× and 40× magnification); F: Single cell induction in Jimson weed suspension in 1 mM Colchicine treatment for 7 days. All samples treated with FDA and PI and examined under Leica fluorescent scope. Note the high viability of the cells seen here in the FDA stain and with very little red stained cells in PI.

Figure 6:
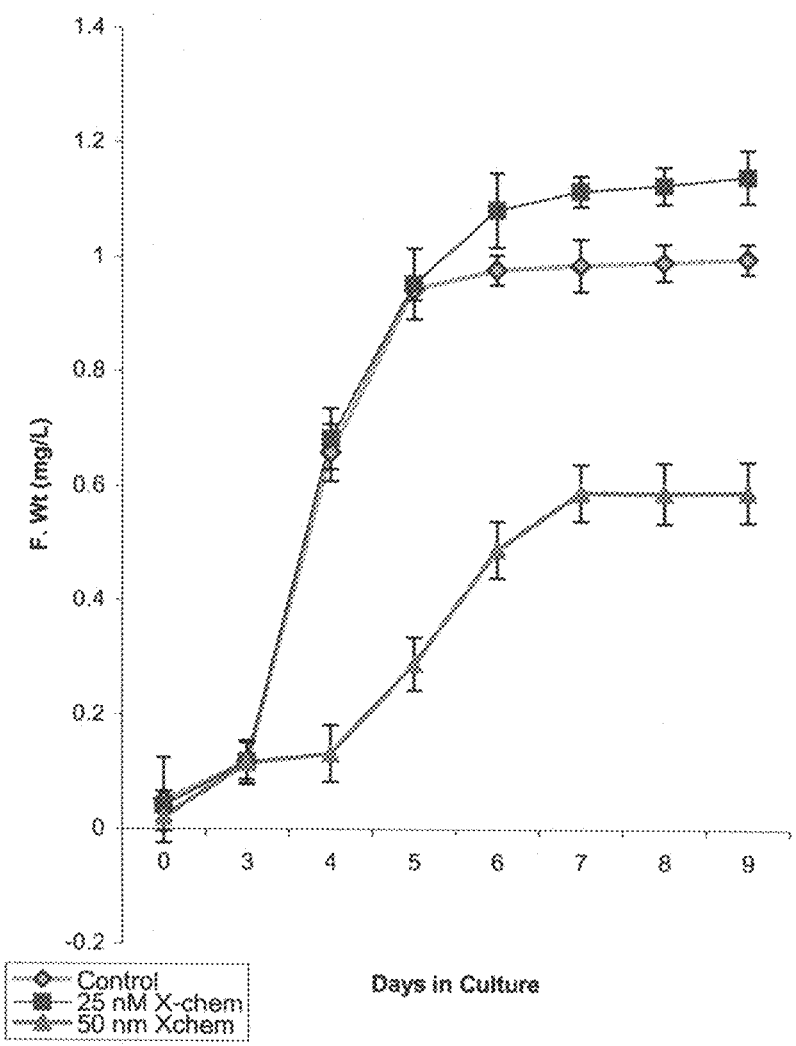

FIG. 6: Effects of DAS-PMTI-1, a Dow AgroSciences (DAS) proprietary methyl indole derivative and a potent microtubule inhibitor herbicide, on NT1 tobacco cell growth. Cells were grown in the absence or presence of 25 or 50 nM DAS-PMTI-1 in NT1B medium with 3% Glycerol as the exclusive carbon source. All fresh weight values represent the means ±0.18 from replicated samples.

FIG. 7: Single cell and colony production from DAS GAD1762-034 suspension lines.

FIGS. 8A, 8B and 8C: 2-6 weeks growth of colonies from DAS GAD1762-034 single cells.

Figure 9:
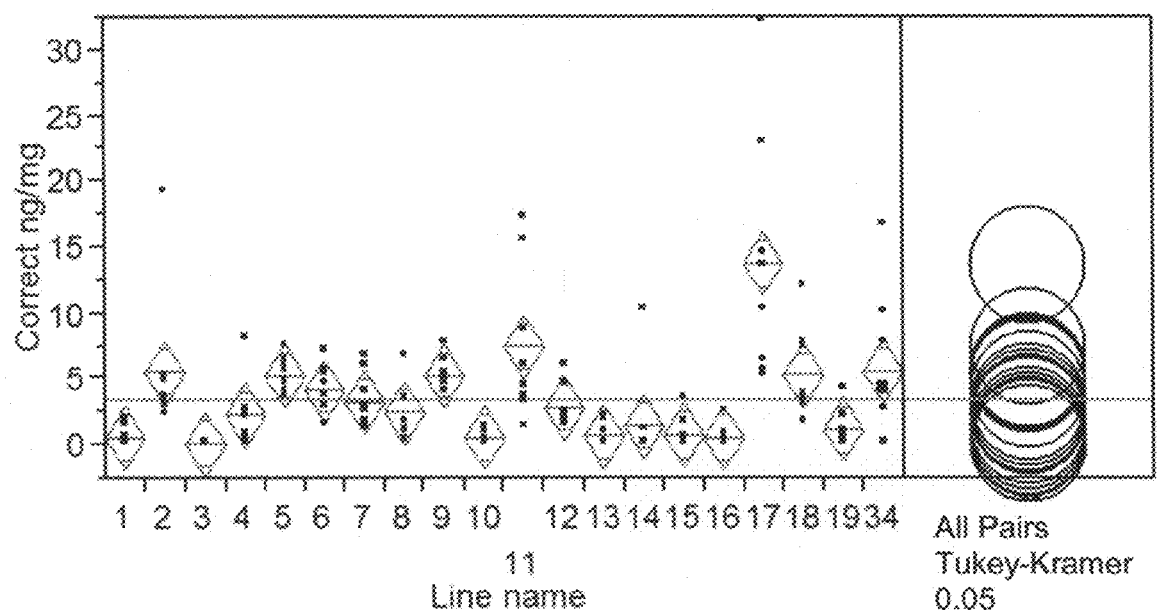

FIG. 9: Collected samples at 7 and 13 days for over 4 subculture cycles and carried out expression analysis. The expression data obtained was plotted.

Figure 10:

FIG. 10: Single Cell BY2 cells that are isolated using DAS-PMTI-1. A 20-50 nM concentration was used to produce single cells after 5 days of sub culture. Note the cells are single cells (the pair has overlapping edges), and the picture was taken under Differential Interference Contrast Scope attached to a confocal imaging system.

Figure 11:
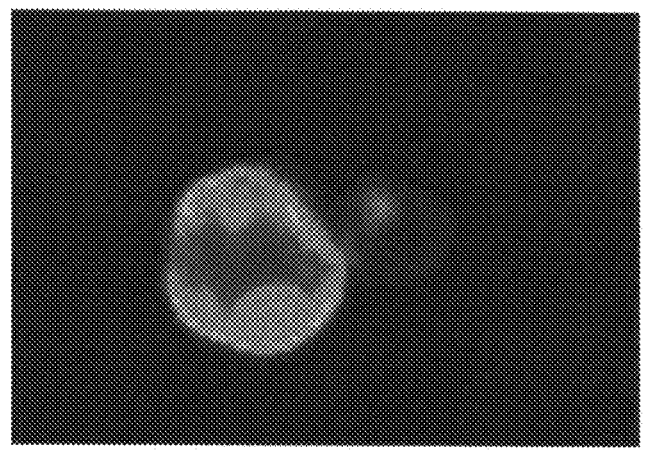

FIG. 11: YFP expression (Ubi10-YFP plasmid) after 72 hrs PEG treatment. One of the small daughter (dividing) cells in the plane of focus shows GFP expression indicating that the expression could be stable.

Figure 12:
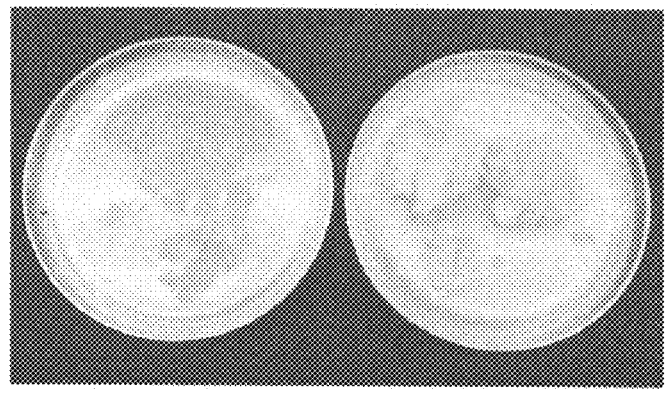

FIG. 12: Left: Untreated control tissue inhibited by 100 mg/L Kanamycin. Right: Single cell derived putative transplastomic isolate growing on the selection media.

Figures 13A, 13B:
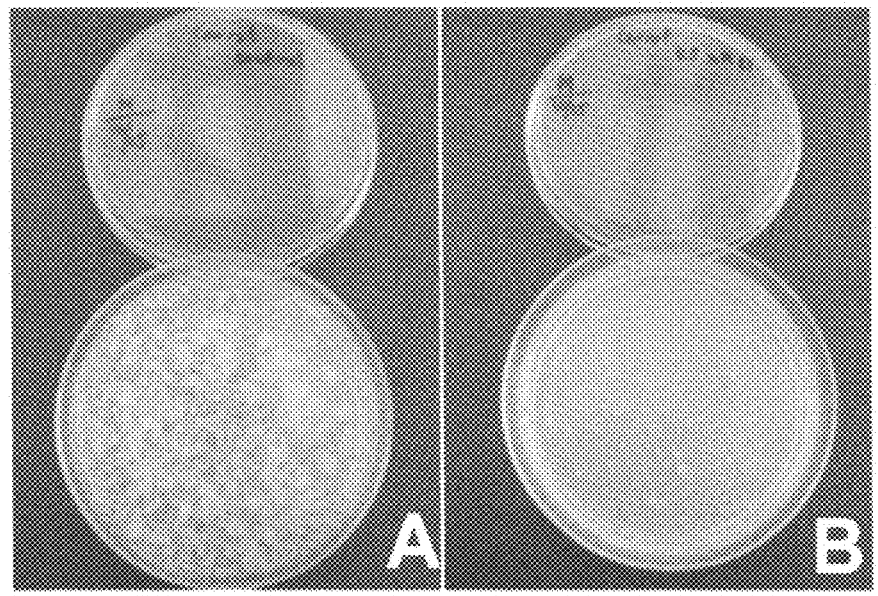

FIG. 13: Production of clonal lines from Carrot single cell suspensions. The lawn growth on the M-medium plated with untreated suspension aggregates (Panel A). The growth of discrete colonies on the medium plated with the single cells (Panel B).

Figure 14:
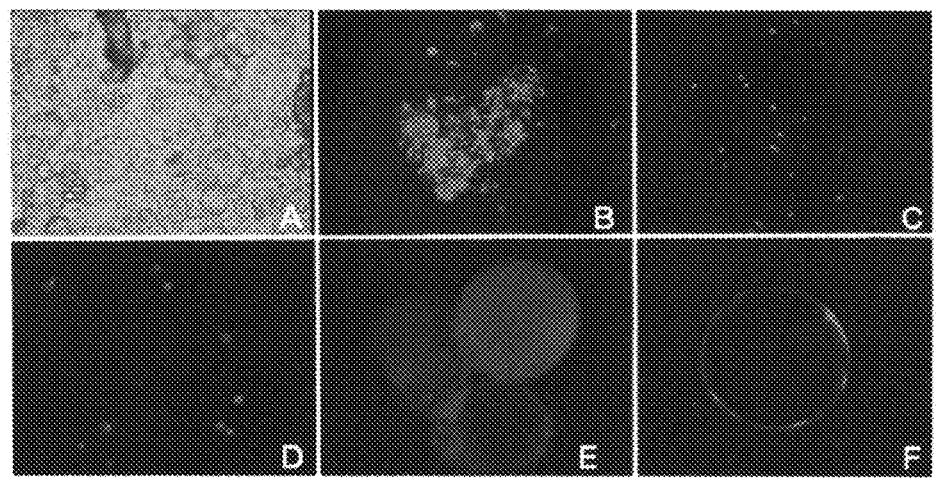

FIG. 14: 0.5-1 mM colchicine treatment in liquid medium and cultures analyzed at 14 d after subculture initiation (end of the second subculture cycle). A: The single cells are released from the clusters; B: Tightly packed cell aggregate stained with FDA vital stain; C and D: FDA stained single cells released in 1 and 0.5 mM treatment respectively, after filtering the suspension (using filters with 100 um diameter pores); E and F: Closer view of the single cells from D.

Figure 15:
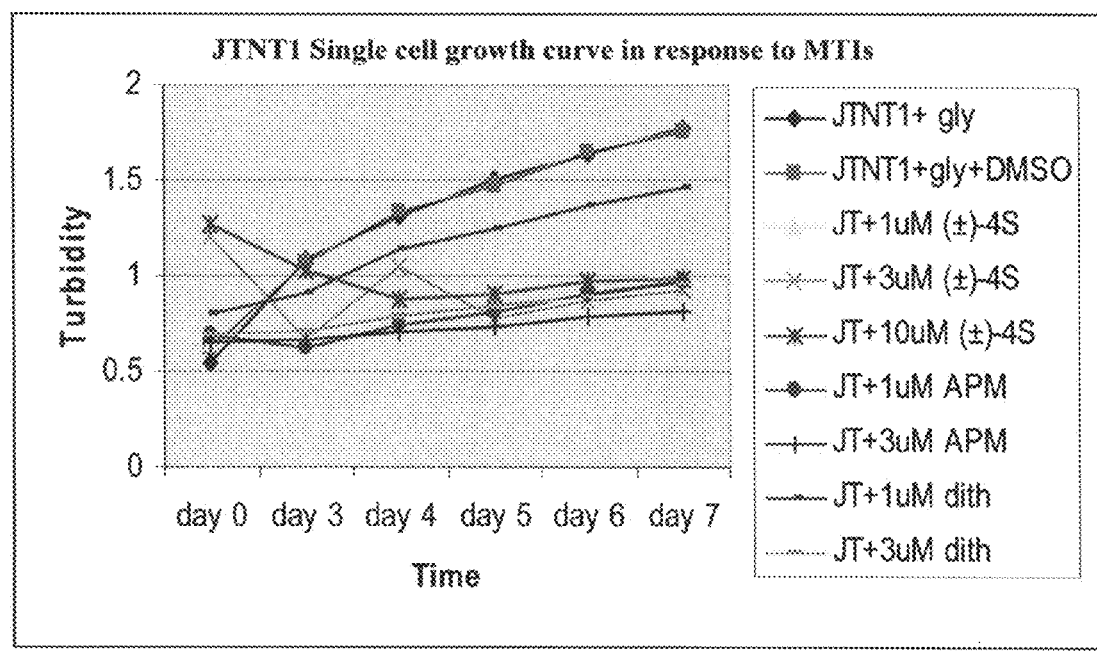

FIG. 15: JTNT1 single cell growth curve in response to MTIs.

DETAILED DESCRIPTION

The ability to isolate and grow single cells has numerous possible applications. For example, methods outlined herein have utility in the improvement of processes related to the productivity of plant cell cultures for animal health applications.

Thus, methods of the subject invention are useful for enhancing process efficiency of animal health and biopharma plant-cell-based products. Embodiments of the subject invention can help in screening of transgenic cell line elite clones, such as in mini suspension cell culture initiation in minimizing batch to batch variation, to develop a Standard Operating Protocol (SOP) for single-cell-based transformation systems to minimize or eliminate non-transgenic cells in aggregates. In summary, aspects of this invention are useful in animal health HTP (high throughput process) screening and host cell line improvement programs.

The subject invention also exemplifies and allows for further development of single cell based assays and cell sorting processes to identify stably expressing cells based on the RNA expression coupled with the cell quenching fluorescent probes.

Such single cells are also useful in site-directed homologous recombination transient screening in the place of the current protoplast-based transient system. Black Mexican Sweet (BMS) maize suspensions and canola suspensions, for example, can provide single systems for such applications. Thus, targeted homologous recombination, for example, can be used in embodiments of the subject invention. This type of technology is the subject of, for example, WO 03/080809 A2 and the corresponding published U.S. application (USPA 20030232410), relating to the use of zinc fingers for targeted recombination. The use of recombinases (cre-lox and flp-frt for example) is also known in the art.

In vitro plant expression systems can be used to produce useful pharmaceutical and animal health recombinant proteins. A key advantage of such plant expression systems is that they are eukaryotic in nature—possessing an endomembrane systems and secretory pathways similar to that of mammalian cells. Therefore, complex proteins are generally folded efficiently and assembled with appropriate post-translational modifications.

Another benefit of plant production systems is the potential for scale-up. Virtually limitless amounts of recombinant protein could be grown either in contained green tissue or scaled-up in industrial facilities using fermentation or bioreactor systems after screening for elite-expressing clones and bulking up such homogenously expressing cell lines.

Two strategies for the production of single cells are exemplified herein. Both successfully worked to separate viable single cells. However, the colchicine method is more preferred to the enzyme degradation method in obtaining a large volume of single cell suspension with intact cell wall at least in two suspension cell types. The enzyme method showed not only inhibition of cell growth, but a higher degree of mortality. Also, when viable cells were plated on the gel medium without removing or rinsing the used medium, the cells died, and no colony growth was observed. It is recommended that the use of such single cell suspensions produced through the enzyme degradation method could be used, but further optimization would be required.

Conversely, addition of tubulin inhibitors like colchicine tested in this study appears to be very useful for separating plant cells and selecting single cells. This method is simple as it involves only addition of appropriate volume of colchicine to the liquid medium during the subculture stage. This will be a pivotal tool which will be of great significance for a given suspension in process such as the initiation of mini-suspension cultures with uniform inoculum of high viable cells as starter cells. The technique could increase the efficiency of electroporation, Whiskers™, and *Agrobacterium* mediated transformation. Such single cells preparation could be also used to isolate elite clones of recombinant protein producing lines from the transgenic suspension aggregates.

Although the protoplast method has been used for single-cell isolation, the subject colchicine method is easier and more powerful. Single cells obtained by the colchicine method are more stable than protoplasts, because of the presence of walls, and do not require the regeneration of cell walls. The cells have walls with a normal composition of the xyloglucan/cellulose network (Hayashi and Maclachlan, 1984). They do not produce callose during cell expansion and separation as seen in the observations where pine seedling cells, elongating in the presence of colchicine, do not have abnormal wall thickening but are enlarged radially (Itoh, 1976). The growth of the cells is normal after subculture in colchicine-free medium, whereas most protoplasts are arrested and reluctant to divide (4). Colchicine-cultured cells may have some degree of polyploidy, however, the concentrations of colchicine used (0.1-1.0 mM) in this study was 10 to 100 times lower than that required (5-20 mM) for the induction of polyploidy. Recovery of single cells has been much better with the colchicine method than with protoplasts (Hyashi and Yoshida, 1988). The subject cells can be further tested using flow cytometry to evaluate the polyploidy level and the genome stability. In addition, increased ploidy levels could provide additional benefit of recombinant protein level enhancement through the increased copy numbers of the transformed cells.

The galacturonan activity showed biological functions of cell separation in soybean suspension cells and are reported as oligosaccharins, because it showed biological functions for cell separation. (Albersheim and Darvill, 1985). Therefore galacturonic acid is also tested in these suspension cells to achieve cell separation with out any ploidy change, just in case there is any colchicine induced ploidy change observed in the single cell suspensions reported here. So, the direct use of galacturonan and other similar oligosaccharins are being further evaluated to compare the efficiency in separating the cells by disrupting the cell adhesive properties. Thus, the subject invention provides simple methods that are reproducible and consistent through several passages of suspension cell cycles, while the cells simultaneously maintain genomic stability.

One preferred compound exemplified herein is DAS-PMTI-1. This compound appears to be very potent (~100-1000× than colchine in affecting the growth of the cultures). After 7 days of treatment there is considerable cell death in a 0.5 mM concentration, but when these cultures were subcultured in the absence of DAS-PMTI-1, PH suspension cells recovered as single cells with a low frequency after 2 weeks. Further optimization can be carried out to determine the preferred concentrations of this compound depending on the preferred applications (such as type of cell and the like) for the separation of single cells. Other MTI inhibitors having similar functions can be used in the subject cell separations by disrupting pectin synthesis. In light of the subject disclosure, additional MTI inhibitors and analogs thereof can be tested and screened for their efficiency in producing and maintaining single cells.

The chemical structure of DAS-PMTI-1, also known as 4-chloro-1,5-diphenyl-1H-pyrazol-3-yloxy)-acetic acid ethyl ester, is as follows:

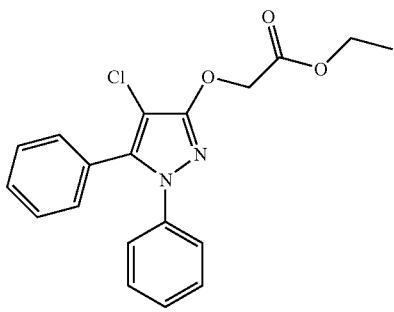

A preferred genus of compounds for use according to the subject invention are DAS-PMTI-1-type compounds. Such compounds can conform to the general structure provided above and include functional (for use according to the subject invention) derivatives and analogs thereof.

Following is a generic chemical formula for some known microtubulin inhibitors for use according to the subject invention. While DAS-PMTI-1 is a preferred embodiment, practically any microtubulin inhibiting agent can be used according to the subject invention. In some preferred embodiments, one or more members of the following diarylpyrazole genus are used in combination with colchicine:

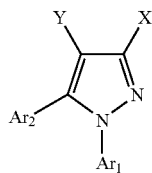

wherein
X=$CO_2R$, $CH_2CO_2R$, $CH_2CH_2CO_2R$, $(CH_2)_3CO_2R$, $OCH_2CO_2R$, $OCH(CH_3)CO_2R$, $OC(CH_3)_2CO_2R$, $CH_2OCH_2CO_2R$, $CH_2CH(CO_2CH_2CH_3)CO_2R$, $OCH(CO_2CH_2CH_3)CO_2R$ Y=CN, Cl, Br, F, $NO_2$ $Ar_1$=unsubstituted phenyl, unsubstituted pyridine, 1-3 substituted phenyl, 1-3 substituted pyridine, substituted with halogen or CN $Ar_2$=unsubstituted phenyl, unsubstituted pyridine, 1-3 substituted phenyl, 1-3 substituted pyridine, substituted with halogen or CN R=H or 1-5 carbon linear or branched ester Thus, single cell plant suspension cultures have been produced using Microtubule Inhibitors, and they can be maintained in culture for at least 2 subculture cycles. These single cell suspensions are unique in that they have an intact cell wall, yet they exist separately from each other.

A "transgenic" plant, plant cell, and the like is (unless otherwise specified) a whole plant, plant cell, plant cell culture, plant cell line, plant tissue culture, lower plant, monocot plant cell culture, dicot plant cell culture, or progeny thereof derived from a transformed plant cell (or protoplast or the like) that contains foreign DNA, introduced by laboratory techniques, not originally present in a native non-transgenic plant cell of the same species. The tennis "transgenic plant" and "transformed plant" have sometimes been used in the art as synonymous terms to define a plant whose DNA contains an exogenous DNA molecule. A transgenic plant may be stably transformed to contain foreign DNA that functions within, and is incorporated into, the genomic DNA of the plant or is a transgenic plant which has been transformed by viral-based vectors and transiently expressed the foreign DNA.

"Isolated" and "purified" imply the "hand of man" and can apply to polynucleotides and proteins. A cloned polynucleotide is an isolated polynucleotide, for example.

Transformation methods. These single cells have been tested for nuclear and plastid transformation using Agrobacterium and Polyethylene glycol (PEG) for nuclear transformation and biolistic bombardment for plastid transformation. In nuclear transformation attempts, the delivery of the plasmid DNA and the Yellow Fluorescent Protein transient expression have been demonstrated. Cells have been recovered in plastid transformation, and stable transformation was shown through PCR analysis. Transplastomic callus isolates were bulked and are being analyzed for the selectable marker, nptII gene expression through ELISA.

The transformation methodology described herein can be applied to animal health processes. However, the single cell based transformation through novel delivery methods including nanoparticle delivery can also provide unique approaches for transforming crop plants in addition to the host of cell types used for recombinant protein production.

The development of the subject single cell transformation through PEG and/or electroporation methods make the single cells with the intact wall as amenable as bacterial/mammalian cell systems, and is also useful in high throughput transformation systems for those cell types.

The ability to transform single cells has numerous possible applications. For example, methods outlined herein have utility in the improvement of processes related to the productivity of plant cell cultures for animal health applications. Again, the subject processes are useful for enhancing process efficiency of animal health and biopharma plant-cell-based products. The subject processes can also help with screening for elite clones of transgenic cell lines. Such applications can be used for mini suspension cell culture initiation in minimizing batch to batch expression variation, and to develop an SOP to minimize or eliminate the non-transgenic cells or the presence of multiple events in aggregates.

As discussed in the Background section, Agrobacterium methods are very inefficient, and WHISKERS™ mediated transformation will not serve as a high throughput process. The PEG mediated method is used with protoplasts. Though tobacco protoplasts are easy to transform, they are not amenable easily for HTP transformation process due to the problems of cell wall regeneration.

In contrast, the subject invention provides an intact cell wall. The PEG-mediated process is the first report of a single cell with an intact cell wall. The subject methods are also highly efficient. Also, this process eliminates backbone integration by using fragment-purified plasmids for transfection. A rapid transformation protocol involving single plant cells through processes such as Fluorescent Activated Cell Sorting (FACS) would be ideal for miniaturization and automation of processes to screen suitable events with reduced cost, resources and timelines. This can drastically improve the current callus or suspension aggregate selection process by screening transformed cells through cell sorters and to determine homogenously expressing elite events for further advancement through industrial research or production pipelines.

Thus, the subject processes provide fundamental foundations for new bioprocessing research and development, for HTP screening for animal health needs and host cell line improvements, for example.

The subject invention allows for further development of single cell based assays and cell sorting processes to identify stably expressing cells based on RNA expression coupled with cell quenching fluorescent probes.

Such single cells are also of use in transient and/or stable screening of Gene of Interest (GOT) for trait and crop protection platforms.

Unless specifically indicated or implied, the terms "a", "an", and "the" signify "at least one" as used herein.

All patents, patent applications, provisional applications, and publications referred to or cited herein are incorporated by reference in their entirety to the extent they are not inconsistent with the explicit teachings of this specification.

EXAMPLE 1

Materials and Methods

BY2 suspension-cultured cells were obtained from Japan tobacco and maintained in LSBY2 medium in a 7 day cycle. Jimsonweed suspension and Pettite Havana tobacco suspensions were initiated from callus initiated at DAS and Xanthi suspensions were procured as a sample from Professor Jack Widholm from UTUC, IL. JT-NT1 suspension cells, obtained from Washington University that are maintained in NT1B medium in 7 day cycle were used only for the pectin degradation enzyme study to separate the cells into single cells. The cells were cultured in shake flasks at 25-28° C. in dark on orbital shakers at 150 rpm. Colchicine was obtained from Fluka, DAS-PMTI-1 (Martin et. al, 2001; Smith et al., 2001), obtained from DAS CRS, and the pectin degrading enzymes (pectolyase Y and pectinase) were from Sigma. Stock concentrations of both the tubulin polymerization inhibitors used in this investigation were dissolved in DMSO to prepare a 0.5 M stock solution. The concentration tested for the pectinase and pectolyase enzymes were in the range of 0.0005% to 0.005%. The tobacco suspension cell lines NT-1 and BY-2, for example, are suitable for the practice of the present invention. BY-2 cells are commercially available and are available according to Nagata et al, for example (Nagata, T., Nemoto, Y., and Hasezawa, S. [1992], Tobacco BY-2 cell line as the "HeLa" cell in the cell biology of higher plants. Int. Rev. Cytol. 132: 1-30). NT-1 cells were originally developed from *Nicotiana tabacum* L.cv. bright yellow 2. The NT-1 cell line is widely used and readily available; though, any tobacco suspension cell line is consistent with the practice of the invention. It is worth noting that the origins of the NT-1 cell line are unclear. Moreover, the cell line appears variable and is prone to change in response to culture conditions. NT-1 cells suitable for use in the examples below are available from the American Type Culture Collection under accession number ATCC No. 74840. See also U.S. Pat. No. 6,140,075.

EXAMPLE 2

Microscopic Observations

Cell expansion and separation were observed by light microscopy (with Nomarski and dark field optics). Spherical cells and single cells were counted by using a hemacytometer to determine the degree of cell expansion and separation, respectively. Cell numbers in aggregates were determined by treating with 5% (wt/vol) chromium trioxide for 16 hr and counting cells (Henshaw et. al, 1966). Cell viability was determined by staining cells (Yokoyama et.al, 1997) with fluorescein diacetate (FDA) and propidium iodide (PI) using a fluorescent microscope (Zeiss Photomicroscope). In order to determine the presence of the cell wall in this single cell cultures optical brightener was used. Calcafluor obtained from Sigma, which is a specific fluorescent dye for cellulose is used in this study, and the cellulose-Calcafluor complexing was observed by fluorescence microscopy (Zeiss Photomicroscope). Calcofluor (Sigma Chemical Co., St. Louis, Mo.) was prepared as a 0.1% (wt/vol) solution in PBS buffer and stored in the dark at room temperature (Kwok et.al, 2003). Prior to use, the Calcafluor stain was centrifuged at 15,000 g for 2 min to remove precipitates. A drop or two of the Calcafluor solution was added to the separated cells. After 2 or 3 min at room temperature, the cell suspension was rinsed with water and counterstained with 0.1% Evan's blue (Sigma; E-2129) in TBS (pH 7.2) for 1 min at room temperature and viewed under a UV microscope at a wavelength of 395 to 415 nm (observation light of 455 nm). The cell wall appeared as bluish-white or turquoise oval halos.

EXAMPLE 3

Results of Continuous Pectinase and Pectolyase Treatments in the Medium

Figure 1:
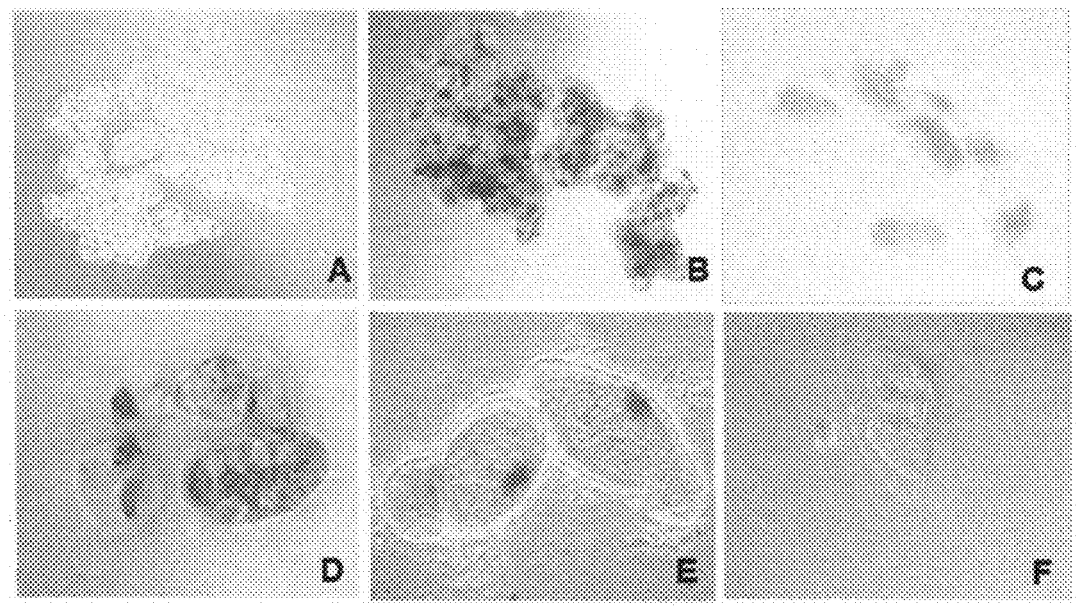
FIG. 1: Single cell isolation of JTNT1 suspension cells with intact cell wall in continuous Pectolyase treatments subcultured in the medium for 7 days.

Petite Havana, BY2 and NT1 tobacco suspensions were used to investigate the effect of pectin degrading enzymes, pectinase and pectolyase at different concentrations. JT-NT1 suspensions did respond to pectinase treatments better and BY2 suspension responded to pectolyase enzyme treatments better than the other enzyme counterpart. However, there was cell mortality as visualized by the vital stains and the inhibitory growth of the cell types. The inoculum volume of cells at the sub culture stage was increased up to 12 times to have reasonable yield of the single cells. PH and the BY2 cells could be cultured for at least 7 days in culture with pectolyase. Continuous culture of these cells in low concentration pectolyase enzyme (3 active units) appeared to be detrimental. The cells at 6th day of culture yielded high single cells when the volume of inoculum was 6 ml (starter inoculum volume at stationary phase) and cultured in a 50 ml fresh medium along with the enzyme. These cells when tested with FDA and PI after 6 days of culture showed a higher degree of viable single cells (FIGS. 1 and 2). The growth of the suspension culture was drastically affected in the enzyme treatments and subculturing the cells in the same enzyme containing medium appeared to be detrimental. It is recommended that the cells could be treated fresh for up to a maximum duration of 7 days in culture and these cells then should be transferred to the medium without the enzyme to recover the growth. At best this method could be used for screening elite transgenic clones in the heterogeneous aggregates or to start high throughput suspension cultures with the uniform cell volume.

FIG. 1: Single cell isolation of JTNT1 suspension cells with intact cell wall in continuous Pectolyase treatments subcultured in the medium for 7 days.

A—Normal BY2 suspension; B—Same as A, but I2KI stained cells to show the aggregation of cells; C and D—Separated cells after 6 days of continuous enzyme treatment; E and F—Separated single cells with and without I2KI staining. Note the normal cell division (F)

FIG. 2: Viability of the BY2 cells 6 d after continuous Pectolyase treatment (cells are treated with FDA and PI) and the yield of single cells.

A: BY2 cell aggregates; B: BY2 in 1 ml inoculum in Pectolyase in the medium for 5d; C: 6 ml inoculum with enzyme in the medium 5 d; D, E, and F: Microscope field snap shots of C; G: control clumps with BY2 cell variant developed in BAP and 12% sucrose; H and I single cells from 5d continuous enzyme treatment from G. Cells stained in FDA and PI. Note the dead cells in PI stained red.

EXAMPLE 4

Effects of Colchicines on the Growth of BY2, NT1, Petite Havana (pH) and Xanthi (Xan) and Jimson Weed (JM) Suspension Cells After 7 days of culture the number of cells of BY2, Xan, and JM cells responded at 0.5 mM and 1 mM concentration of colchicines (FIGS. 3, 4, and 5). However, a high degree of single suspension cells were seen in 1 mM of BY2 suspension cells and JM cells. It was significant to note that the JM cells growth was drastically affected even in 0.5 mM colchicine and the growth could not be recovered even after additional week of growth in the same medium. This indicates that cell division is inhibited by colchicine in JM cells and lower concentrations need to be tested further to optimize the cells separation without a reduction in the culture density or growth. Interestingly, such a growth inhibition was not observed by BY2 suspension cells that could be grown for at least 14 days continuously in the presence of 1 mM colchicine. Cell swelling was first observed on the 3rd day, and the cells developed spherical shapes as culture continued in BY2 suspension cells. Since the spherical cells were gradually released from aggregates, the cell separation presumed to be accompanied by the cell expansion. There are about equal amounts of BY2 cells in medium containing 1 mM colchicine after 7 days as in control cultures. When cells cultured for 7 days in 1 mM colchicine were sub-cultured to a colchicine-free medium, the ability to grow as aggregates was not completely recovered instead ~90% of the suspension cells were seen as single intact cells. Cell expansion and separation also partially occurred in cell suspension aggregates of all the other cell suspensions tested in medium containing 0.5 mM colchicine. There is inhibitory cell growth response observed in JT-NT1 and JM suspension cells. NT1 suspension cells recorded almost 50% reduction in growth in 1 mM Cochicine.

Large segregated cells were observed in these cells similar to those of separated epidermal root cells reported in the qual-1 pectin mutants (Bouton, 2002). Similar partial segregation of cells with general spherical shape was observed in all the cell suspension types tested with the DAS-PMTI-1. However, the cell growth was affected very significantly in the DAS-PMTI-1 treated suspension in 0.5 mM concentration. Further experiments can be carried out to optimize conditions of cell separation with this compound and to minimize cell inhibitory growth. As demonstrated by FDA and PI stain tests, there is a high degree of cell viability in the BY2 and JM cell suspension tested. The cells were highly rounded and in many cells showed a beak like projection indicating the cell wall extension of active cells, possibly before cell division. The separated cells were large, expanded and had a spherical shape that is typical of protoplast. Calcafluor stain was used to determine the presence or absence of the intact cell walls. FIG. 4. Shows clear presence of the cell wall around these round cells. Observation of these cells under dark field condenser of the scope showed thick cell wall around the cell (FIG. 3: panel C). These single cells were resilient in the shake cultures as there were no dead cells due to the absence of the pectin and the presence of large cells as seen in the vital stain test (FIG. 5). A very high percentage of live healthy cells were seen as seen in this panel. Therefore, it is possible to use these cells in shake cultures or in micro-well plate as inoculum with precise number of the cells.

FIG. 3: Single cell suspension induction from 7d Colchicine treatments in the medium from the cell aggregate suspensions of BY2 and Xanthi tobacco suspension.

A: Normal BY2 suspension aggregate (Calcafluor stained); B: Single Cell BY2 suspension in 1 mM Colchicine for 7d; C: Same as B, but enlarged to show single cells with intact walls; D: Suspension aggregates of Xanthi; E: Xanthi suspension aggregates treated for 7d in 0.5 mM Colchicine. Note the partial release of single cells in 0.5 mM; and F: Separated single cells of Xanthi in 1 mM Colchicine.

FIG. 4: Single cell release with intact cell walls in Colchicine treatments from BY2- and Xanthi tobacco suspension aggregates.

A: Normal BY2 suspension aggregates B: Single Cell BY2 suspension in 1 mM Colchicine for 7d; C and D: Recovery of cells back to aggregates after removal of Colchicine (4d after subculture with 1 culture cycle of colchicine treatment); E: Suspension aggregates of Xanthi; F: Xanthi suspension aggregates treated for 7d in 1 mM Colchicine. Note the released single cells in BY2 and Xanthi cultures and the presence of the intact cell wall as seen in the presence of the optical brightener, Calcafluor. (All samples treated with 0.1% of Calcafluor and examined under Leica fluorescent scope).

FIG. 5: Single viable cell release with intact cell walls in Colchicine treatments from BY2-Variant tobacco (habituated in EP 12% sucrose medium) and Jimson weed suspension aggregates.

A: Normal BY2-V suspension aggregates B: Closer view of the untreated aggregates; C, D and E: Single Cell BY2 suspension induction in 1 mM Colchicine for 7d (Cells under 10×, 20× and 40× magnification); F: Single cell induction in Jimson weed suspension in 1 mM Colchicine treatment for 7d. All samples treated with FDA and PI and examined under Leica fluorescent scope. Note the high viability of the cells seen here in the FDA stain and with very little red stained cells in PI.

EXAMPLE 5

Production of Single Cells and the Influence of DAS-PMTI-1 in Medium Containing Glycerol as the Sole Carbon Source The subject Example provides another discussion regarding novel glycerol growth medium and the DAS-PMTI-1 low concentration effect, and growth characteristics. The subject results are very significant, as there were prior reports in the literature that glycerol mitigates. Colchicine effects in disrupting soybean microtubules; thus, the art taught against the use of glycerol in media for the subject applications. See e.g. Hayashi and Yoshida, 85 PNAS 2618-22 (1988). In addition, the subject glycerol data is new for plant cells, and such results have not been reported previously. Three different genotypes of tobacco rapid cultures have been growing successfully for several months using 3% glycerol as the only carbon source.

This Example also provides a growth curve graph depicting the culture behavior in two different concentrations of DAS-PMTI-1, and it is compared with the null treatment.

Several classes of compounds that disrupt microtubules produce single cells. The compounds include microtubule disruptors or inhibitors (α- and β-tubulin binding compounds) that are classified under (i) dinitroanilines (Colchicines, Oryzalin, Trifluaralin, Chloralin) and (ii) N-phenylcarbamate such as the benzamide, pronamide, the phosphoric amide, amiprophosmethyl (Morejohn and Foskett, 1986; Akashi et al., 1988), as well as the antifungal, benzamide zarilamide (Young, 1991), (iii) the anticancer drug, paclitaxel (Morejohn and Foskett, 1986), vincristin, vinblastin and, (iv) other compounds that disrupts both microtubules and or the wall properties such as cellulose synthesis inhibitors and the cytoskeleton inhibitors such as Aluminum and Coumarin are also tested for their ability to produce single cells with no or low micro-nuclei formation. The Cortical microtubules and the mitotic microtubules have different sensitivity and combination of the compounds from the different classes listed above or from one of the classes but selectively disrupt the tubules to the extent that the cell division is not affected but the cell adhesive property will be sufficiently disrupted to achieve and maintain the cells in single cell stage with low or no genomic instability.

The effects of Microtubule inhibitors (MTI) on tobacco cell growth in suspension culture were examined. Day seven stationary phase cells (1 ml) were transferred to medium (50 ml) in 250 ml shake flasks (Bokros et al., 1993) containing different concentrations (25 to 1000 nM) of MTI and were grown in cultures for 7 days in dark at 25° C. Both the control and MTI-containing flasks contained a final concentration of 0.5-0.1% (v/v) DMSO. The growth of these chemicals was evaluated in EP12 medium for BY2 cells and NT1B medium for BTI-NTI cells were the carbon source is substituted with 3% glycerol. The response of these cells was compared with the same medium composition but with 3% sucrose as the Carbon source. The glycerol medium was used since glycerol is known to be microtubule stabilizers and the tobacco cells habituated in 3% glycerol showed no phenolics under stress.

At 1-day intervals triplicate samples (0.5 ml) of cells were sedimented by brief centrifugation in tared microfuge tubes, and fresh weights were determined. The results presented in FIG. 6 show that following a 2-d lag phase, control cells grew rapidly for 4 d and entered stationary phase by d 6. Tobacco cells grown with 25 nM DAS-PMTI-1 showed growth kinetics similar to those of the control culture. However, the fresh weights of these cultures were slightly greater, than the controls during the stationary phase, suggesting a promotion of growth with 50 nM DAS-PMTI-1. Cells grown with 0.5-1.0 mM DAS-PMTI-1 exhibited complete inhibition and cell death within 3 days of culture initiation when examined the FDA and Propidium iodide treated cell under the fluorescent scope. The data demonstrates tobacco cell growth to be inhibited near the threshold of 50 nM, but over 100 nM concentrations causing inhibition of mitosis, and cell death.

Unlike Colchicine, a low potent dinitroanilines for the production of single cells, where 0.25-0.5 mM concentration is effective, DAS-PMTI-1 is very effective at concentrations as low as 5-25 nM even in the presence of glycerol as total carbon source for both NT1 and BY2 cells. The 25 nM concentration range is not only effective in releasing single cells, but also very efficient in not lowering the growth rate of the cells over a period of 10 days (FIG. 6). In fact there is a slight enhancement of the biomass at the stationary phase of the growth owing to the fact that these single cells undergo expansion. However, the microscopic observations did not show the presence of micro-nuclei in these single cells.

FIG. 6: Effects of DAS-PMTI-1 on NT1 tobacco cell growth. Cells were grown in the absence or presence of 25 or 50 nM DAS-PMTI-1 in NT1B medium with 3% Glycerol as the exclusive carbon source. All fresh weight values represent the means±0.18 from replicated samples.

The single cells status of the cells produced through the DAS-PMTI-1 were analyzed under confocal microscope, and they were clearly confirmed to be single cells as the cells were not found to be attached.

EXAMPLE 6

Deconvolution of Transgenic Suspension Lines and Clonal Line Production

Tobacco suspensions normally contain cells in aggregate or small clusters, and they are highly heterogeneous. The cells in culture may be genetically identical (homogenous population) or may show some genetic variation (heterogeneous population). A homogenous population of cells derived from a single parental cell is called a clone. Therefore all cells within a clonal population are genetically identical and highly homogeneous in terms of the cellular character. BY2 and NT1 tobacco cell suspensions are routinely used as model systems in many laboratories.

These cells are readily transformed after removing the cell wall (Mathur and Koncz, 1998), directly via particle bombardment or cocultivation with *Agrobacterium tumefaciens* (An, 1985; Klein et al., 1988; Rempel and Nelson, 1995). Although *A. tumefaciens*-mediated BY-2 transformation is performed routinely in many laboratories, we found that the efficiency in obtaining transgenic calli varies between experiments and mainly depends on the quality of the BY-2 cell culture. Synchronization, BY-2 cells in M and early G1 phase are 10-fold more susceptible for stable *A. tumefaciens*-mediated transformation than to cells residing in G2. In addition, the *Agrobacterium* strain LBA4404 that expresses constitutively the virG gene (van der Fits et al., 2000) is 2- to 5-fold more effective in generating transgenic calli. Typically, about 500 transgenic calli can be obtained from 4 mL of BY-2 cells cocultivated with this *Agrobacterium* strain, allowing phenotypic screening programs to be performed. However, the clusters or aggregates of the transform suspension lines appear to have heterogonous multiple transgenic events. As a result, there are inconsistent expression levels from one batch culture to another. The single cell method is employed to deconvolute the chimeric mixture of cells in the cluster and separate them as individual cells to identify clonal events. Single cells were produced from the chimeric transgenic suspension NT1 tobacco lines (GAD 1762-034) transformed with PAT selectable marker gene (FIGS. 7 and 8).

FIG. 7: Single cell and colony production from DAS GAD1762-034 suspension lines. FIGS. 8A, 8B and 8C: 2-6 weeks growth of colonies from DAS GAD1762-034 single cells.

About 20 discrete colonies were randomly picked and bulked further on a fresh selection medium. Suspension lines were produced from these colonies and rapidly growing lines were obtained through 6 sub-culture cycle of 7 days each. The biomass productions of these colonies were rather uniform across these lines and advanced 19 lines for further protein analyses.

Collected samples at 7 and 13 days for over 4 subculture cycles and carried out expression analysis. The expression data obtained was plotted (FIG. 9).

It is clear from the data analysis that there were several clonal lines with tight expression over several subculture cycles could be obtained when compared to the control suspension aggregate line # 34. In addition the subline 17 out performed the control line in expression levels indicating that this process will pick up the clonal elite line in the population and further reformed deconvolution could help obtain uniformly expressing elite lines.

EXAMPLE 7

Transformations of Single Cell Suspension Cultures

Material and Methods

Preparation of plant cell material: Three to 4 days prior to transformation, a 1-week-old suspension culture is sub-cultured to fresh medium by transfer of 2 ml of NT1 or BY2 culture into 40 ml NT1B or LSBY2 media in a 250-mL flask. The concentration of the Microtubule inhibitors (MTI) were used as described above to produce single cells. The single cells were collected either at 4 days or 7 days after the MTI treatment.

FIG. 10: Single Cell of BY2 cells that are isolated using DAS-PMTI-1, a DAS proprietary Methyl indole derivative and a potent microtubule inhibitor herbicide. A 20-50 nM concentration was used to produce single cells after 5 days of sub culture. Note the cells are single cells (the pair has overlapping edges), and the picture was taken under Differential Interference Contrast Scope attached to a confocal imaging system.

When the BY2 single cells were processed through the Beckman Flow cytometer, there were 658250 viable cells/ml of medium viable cells with a mean diameter of 10.43 um and a volume of 593.8 um3.

*Agrobacterium* preparation: The *Agrobacterium tumefaciens* strain LBA4404 containing the YFP gene (pDAB4613) construct is stored in 50% glycerol at −80° C. A 20-500 µl aliquot of the stock culture, containing the expression vector is used to initiate a liquid culture directly by adding 20-500 µl to 30 ml YEP liquid media containing 10 g/L yeast extract, 10 g/L peptone, 5 g/L NaCl, 10 g/L sucrose and 50 mg/L spectinomycin. Following incubation for 18-20 hrs in the dark at 28° C. and 150-200 rpm until the culture reaches a density of ca. OD600 was 1.5.

Co-cultivation of single cells for nuclear transformation: At the time of transformation, 1.0 ml of *Agrobacterium* suspension is added to a flask containing 40 ml of the 4 or 7-day old tobacco single cell suspension (pre-washed in the medium to remove any MTI) and mixed by pipetting up and down 5 times using a 10 ml wide-bore pipet. The uniform suspension is then transferred in 250 µl aliquots into 24-well plates wrapped in parafilm and cultured in the dark at 25° C. without shaking for 3 days. Test an aliquot of about 50 µl of suspension by placing it on the microscopic slide and looking for Yellow Fluorescent Protein (YFP) transient expression.

PEG/DNA treatment of single cells for nuclear transformation: JT-NT1 cells aggregates suspensions were treated with 1 mM final concentration of Colchicine (Fluka) in NT1 B medium at the subculture initiation and cultured for 7 days at 125 rpm on an orbital shaker. The suspensions were cultured at 25° C. At the end of the seventh day 1 ml (0.6 OD600) of single cells were collected from the flask and dispensed into a 14 ml sterile tube. Add 10 ml of MaMg medium (for Composition see Table 1 below) and spin 5 min at ~1000 RPM.

TABLE 1

MaMg medium Composition (PEG mediated transformation)
MaMg medium

| Total Volume of the medium | Stock Conc. | 100 ml |
|---|---|---|
| MES | | 0.1 g |

TABLE 1-continued

MaMg medium Composition (PEG mediated transformation)
MaMg medium

| Mannitol | | 7.3 g |
|---|---|---|
| MgCl$_2$ | 15 mM | 1.5 ml |
| PH 5.5 | | |

Decanted liquid and re-suspended cells in 300 µl MaMg and add ~50 µg plasmid DNA. To this single cell and DNA mixture, added 300 µl. PEG 3350 (40% PEG 3350 w/v, 0.4M Mannitol, 0.1M Ca (NO$_3$)$^2$ pH 5-6 final) slowly and mixed it gently. Incubated the single cell, DNA and PEG mixture at room temperature for 20 minutes and then added 10 ml W5 (wash medium) and spun 5 min at ~1000 RPM. Decanted liquid and added 2 ml base liquid medium (NT1B) and transfer cells suspension in a multi-well plate. Several replicates could be thus transferred in to the wells of 24-well plates. Assayed at 20-24 hours for YFP transient expression by taking a 50 µl volume of cell suspension on to a microscopic slide and then examining them under a fluorescent scope with an appropriate filter (Excitation 500/20 nm, diachrome, emission 535/30 nm)

Biolistic bombardment of single cells for Plastid transformation: The BY2 Cells were treated in 20-50 nM DAS-PMTI-1 in EP12% medium, to increase the number of plastids and with either no 2,4-D of with addition of BAP to increase the size of the plastid for 7 days. At the end of the seventh day the single cells were collected and 2 ml suspension were transferred to the filter paper. The cells were kept on the LS BY2 gel medium for 2 hrs for desiccation. Shot five plates from 2,4-D deficient single cell lnes and BAP treated cell lines each. These cells were treated with 50 nM DAS-PMTI-1 for 2 weeks and on the 3rd week they were in 20 nm DAS-PMTI-1. The cells were fine and relatively healthy.

The cells were bombarded with pDAB3969 on 0.6 µm gold particles following the standard protocol using the biolistic gun (BioRad). They were transferred to LS-BY2 12% sucrose+100 mg/L Kanamycin selection after 2 days of recovery on media without the selection agent.

Results and Discussion.

Nuclear Transformation efforts: The attempts on the PEG (FIG. 11) and Agro transformation (FIG. 3) clearly showed expression frequency similar to each other. In a 50 µl aliquot of cells analyzed there were 2-3 YFP expressing cells. Thus there is one transformed cell in a batch of every 10970 single cells roughly indicating that the process may be not very efficient. It is likely that the cells were not removed of the residual Colchicine and in a parallel experiment, the cells were revived into colonies faster and healthier with a higher frequency of colonies. This indicates a washing step increases the transformation frequency in optimization experiments. If only one event will be picked up from a single cell, there will be at least 50-60 transformed cells per ml of single cells in a micro-well plate in both these transformation methods. However, conditions for transformation can be further optimized, and additional, stably transformed colonies can be isolated.

FIG. 11: YFP expression (LTbi10-YFP plasmid) after 72 hrs PEG treatment. One of the small daughter (dividing) cells in the plane of focus shows GFP expression indicating that the expression could be stable.

Plastid Transformation: After 6 weeks of culture, 5 actively growing colonies were identified on the selection medium. However, the control non treated cells were killed in the 100 mg/L Kanamycin selection (FIG. 12). The actively growing colonies were sampled and are analyzed by PCR to determine the integration of plasmids. Two out of 5 colonies show clear PCR product indicating that the transgene is integrated in the plastids.

FIG. 12: Left: Untreated control tissue inhibited by 100 mg/L Kanamycin Right: Single cell derived putative transplastomic isolate growing on the selection media.

Further experiments are being carried out to further develop high throughput nuclear and plastid transformation protocols.

Further transformation experiments are being carried out to optimize the protocol to further develop a HTP and a backbone-free (using fragment purified plasmid) transformation protocol for new bioprocessing research and development.

EXAMPLE 8

Habituation of Suspension Cultures in Glycerol Medium

Material and Methods.

Conditioning of cultures for synchronization. To improve synchronization, all the cultures were continued for 2 weeks without subculture, followed by dilution of 1 ml of old culture in 50 ml of fresh medium. Undifferentiated and dividing cells were counted 2 days after that subculture (amitotic index of up to 40% was observed), while differentiated non-dividing cells were observed after 10 days of culture. Samples of 0.5 ml of suspension were used for whole mount procedures.

Cell Cultures.

Long-term Bright Yellow-2 (BY-2) cultured in LSGS-BY2 medium (Appendix 1), and NT1 cells and short-term Petite Havana (PHL) tobacco suspension cells were cultured in LSG-BY-2 medium (Appendix II) or in G-NT1 medium (Appendix III). All media had glycerol as substituted carbon source for sucrose in the growth medium except in the case of regular BY2 cultures where the medium in addition to glycerol had 1% sucrose. Suspension cultures were diluted at weekly intervals (1 ml of old culture in 50 ml of fresh medium) in 250 ml Erlenmeyer flasks. The cell suspension was agitated on a rotary shaker at 100 rpm and maintained at 25.0 and in the dark. Vos et al., "Microtubules become more dynamic but not shorter during preprophase band formation: a possible 'Search-and-Capture' mechanism for microtubule translocation," *Cell Motil Cytoskeleton* 57:246-258, 2004).

Characteristics of Cell Cultures Grown in Glycerol Medium.

General growth of all cultures was reduced when compared to the sugar grown control cultures. However, when the initial level of culture inoculums are increased normal growth rates were obtained. The cells were healthy and it was possible to continue to grow them up to 2 weeks in cultures without the typical browning of cells observed in the sugar control cultures. The cells grown in the glycerol cultures had a higher aggregation of cells in the suspension units when compared to their sugar cultured counterparts. These cells were used in the experiments to test the MTI compounds to disrupt the cell adhesive properties of the aggregated subunits as glycerol mitigates the stability of membranes.

Appendix I.

LSGS-BY2 medium consists of Murashige and Skoog macro and micro-salts (Murashige and Skoog 1962) supplemented with 30 ml glycerol (v\v) and 10 g sucrose (w/v), 100 mg/l myoinositol, 200 mg/l KH2PO4, 1 mg/l thiamine and 0.2 µg/l 2, 4-dichlorophenoxyacetic acid. The medium is adjusted pH 5.8 before autoclaving.

Appendix II.

LSG-BY2 medium consists of Murashige and Skoog macro and micro-salts (Murashige and Skoog 1962) supplemented with 30 ml glycerol (v\v), 100 mg/l myoinositol, 200 mg/l KH2PO4, 1 mg/l thiamine and 0.2 µg/l 2,4-dichlorophenoxyacetic acid. The medium is adjusted pH 5.8 before autoclaving.

Appendix III.

G-NT1 medium consists of Murashige and Skoog macro and micro-salts (Murashige and Skoog 1962) supplemented with 30 ml glycerol (v\v), 100 mg/l myoinositol, 180 mg/l KH2PO4, 1 mg/l thiamine and 2 mg/l 2,4-dichlorophenoxyacetic acid. The medium is adjusted pH 5.8 before autoclaving.

EXAMPLE 9

Single Cell Production from Suspension Cultures of Dicotyledons (Tobacco (BY2, NT1, Petite Havana, Xanthi)), Carrot (*Daucus carota* L. ssp. *sativus* cv Sativa)

Carrot Suspension Cultures.

Carrot callus cultures have been initiated from the in vitro maintained *Daucus carota* L. ssp. sativus cv Sativa plants. Isolated leaf petiole explants were cultured on semi solid medium (Mashayekhi-Nezamabadi, 2000). Suspension cultures were initiated from the callus by transferring 50 mg of friable callus in 1.5 ml of LSBY2 medium (Appendix I) in 24 micro well plate. The fastest growing suspensions were then transferred to flasks with 1 ml suspension in 35 ml LSBY2 liquid medium. The cultures were maintained in diffused light in a 7 day sub culture cycle. These cultures were regenerable and the suspension units were chunky with compactly arranged cells. When treated with 0.5 mM to 1 mM Colchicine or with 25 nM to 0.5 mM DAS-PMTI-1 ((4-Chloro-1,5 diphenyl-1H-pyrazol-3 yloxy)-acetic acid ethyl ester) at the suspension intiation stage of the sub culture, the cells from the units separate and release into the medium within the 3rd day of culture initiation. The cell cultures showed homogenous production of single cells in colchicine treatments, but in DAS-PMTI-1 showed single cell production but with assorted cell shapes rather than being round. The cells have intact cell walls as analyzed by the calacafluor stain under fluorescent microscope.

Clonal Line Production of Carrot Single Cell Suspensions.

The single cell suspension at the stationary phase of growth, 7 days after culture initiation in 0.5 M colchicine treatments were diluted using LSBY2 fresh medium to 0.6 $OD^{660}$. A 1.5-ml diluted single cell cultures were plated on M-medium (Appendix H) in 15×100 Petri-plates and spread out using the loop. Untreated carrot suspension aggregates were also diluted to the same density and plated similarly to compare the growth responses between these cultures. After 4 weeks growth in the dark, the plates with the single cells produced several discrete colonies indicating clonal lines could be obtained from these cells. However, the untreated suspension showed a lawn growth of callus on the surface of the plate (FIG. 13). Thus it is possible to show the isolated cells of carrot could produce colonies that are derived from individual cell to produce clonal lines.

FIG. 13: Production of clonal lines from Carrot single cell suspensions. The lawn growth on the M-medium plated with untreated suspension aggregates (Panel A). The growth of discrete colonies on the medium plated with the single cells (Panel B).

EXAMPLE 10

Single Cell Production from Suspension Cultures of Monocotyledons (Maize, Rice (T309), Orchard grass, Wheat (Anza))

Totipotent Chlorophyllous Maize Cell Cultures.

The maize photoautotrophi cultures were initiated and maintained in 7 day culture cycles (Jayakumar et. al. 2005). The cultures were treated at the time of subculture with either 25 nM to 0.5 mM DAS-PMTI-1 ((4-Chloro-1,5 diphenyl-1H-pyrazol-3 yloxy)-acetic acid ethyl ester) or 10 nM to 0.5 mM Trifluralin to separate single cells from the aggregates. Colchicine is active only in concentration above 0.5 mM to a range of 1 mM and released single cells (FIG. 14). The maize suspension units are tightly packed into hard cell aggregates when compared to the dicot cells analyzed. However, the green maize cells suspension had the hardest suspension units and the treatments showed up to 50% of viable single cell release in 7 days that could be either separated by brief spins at 100 rpm or filtering through screens with pores ranging from 75-100 uM diameter.

FIG. 14: 0.5-1 mM colchicine treatment in liquid medium and cultures analyzed at 14 d after subculture initiation (end of the second subculture cycle). A: The single cells are released from the clusters; B: Tightly packed cell aggregate stained with FDA vital stain; C and D: FDA stained single cells released in 1 and 0.5 mM treatment respectively, after filtering the suspension (using filters with 100 um diameter pores); E and F: Closer view of the single cells from D.

Orchard Grass and Rice (T309) Suspension Culture.

Orchard grass and T309 callus were initiated from mature seeds (DAS seed collection) on the semisolid medium. The suspension cultures were initiated from this seed derived callus using the protocol described by Fauquet et. al., 1996. The suspension cell cultures were maintained on a 7 d subculture cycle in shake flasks at 150 rpm in dark. MTI compounds similar to those described for maize (above)were used at similar concentration range. Orchard grass and rice single cells were released 3-5 days after culture initiation. Wheat (cv. Anza) Suspension Culture.

Anza wheat callus were initiated on semi solid MS2-D Wheat medium (Appendix III) from the scultellum tissue. The scutellar tissues were isolated from sterilized and soaked tissues and the callus induced from different tissues was transferred to liquid MS-2D Wheat medium (Appendix III). One fast growing cell suspension lines were isolated and further sub cultured for 7 years on a subculture cycle of 7 days on MS2D liquid medium and maintained long term (7 years). For single cell production the cultures were first habituated in NB dicamba liquid medium (Appendix IV). Anza wheat cultures could be conditioned to produce fine suspensions in this medium with uniform size of cell aggregate units. Colchicine, Trifluaralin or DAS-PMTI-1 was added to the inoculums at the subculture initiation stage into the medium at 25 nM to 1 mM concentration range. The suspension released single cells into the medium from 3 days after culture initiation. The single cells were small and uniform.

Appendix I.

LSBY2 medium consists of Murashige and Skoog macro and micro-salts (Murashige and Skoog 1962) supplemented with 30 g sucrose (w/v), 100 mg/l myoinositol, 200 mg/l KFI2PO4, 1 mg/l thiamine and 0.2 tag/l 2,4-dichlorophenoxyacetic acid. The medium is adjusted pH 5.8 before autoclaving at 120° C. Suspension volume at the $7^{th}$ day of culture, at stationary phase was used to initiate cultures. A 1-ml volume of carrot suspension inoculums is transferred into 50 ml LSBY2 medium and then the cultures were placed on shakers at 150 rpm in the dark at 28° C. The MTI compounds used were added along with the fresh medium at the culture initiation cycle.

Appendix II.

M-medium consists of LS basal salts and B5 vitamins, 30 g of glucose, 1 uM each of 2,4-D and Kinetin, and the medium was adjusted to pH 5.8 before 8 gm/L Noble agar was added to the medium. The medium is then autoclaved and poured into 15×100 Petri plates.

Appendix III.

MS2D medium consists of MS salts ((Murashige and Skoog 1962) and Eriksson's vitamins supplemented with 2 mg 2,4-D, 0.5 mg thiamine, 30 g sucrose, 400 mg myoinositol, 400 mg casein hydrolysate (ECH). The cultures were autoclaved after adjusting the medium pH to 5.8. Suspension cultures were routinely sub-cultured at 7 d intervals (6 ml initial inoculums of used suspension in 54 ml fresh medium) and grown with shaking at 150 rpm in the dark at 28° C. Under these conditions, cell populations were always in exponential growth between 2 and 6 d after inoculation. For the gel medium to induce callus from the mature seed scutellum MS2D medium contained an additional component of Gelrite at 2.5 g/L that is added after adjusting pH.

Appendix IV.

NB dicamba medium consists of NB basal salts, sucrose 30 g/L, myo-Inositol 100 mg/L, ECH casein hydrolysate (ECU) 300 mg/L, L-proline (2.5M) 1.7 ml/L, L-glutamine 500 mg/L, and 6.6 mg/L Dicamba. The medium is adjusted pH 5.8 before filter sterilization.

EXAMPLE 11

Carrot Single Cell Production and Si—C Whiskers Mediation Genetic Transformation of Carrot Single Cell Suspension Cultures Initiation of Carrot Single Cell Suspensions.

A regenerable carrot cryopreserved line (D2-40-018) was thawed and cultured in Linsmeier-Skoog (LS) medium (Nagata, T., Nemoto, Y., and Hasezawa, S. (1992) Int. Rev. Cyto 132, 1-30). Medium salts were purchased from PhytoTechnology Laboratories, Catalog #L689. An actively growing suspension line was established within a week, and the maintenance line was sub-cultured by transferring 2 ml PCV to 58 ml of LS BY2 suspension medium at 28° C. on an orbital shaker (Innova-3300) at 125 rpm under diffused light on a 7 day culture cycle. For single cell production, 1 ml PCV of carrot suspension at the stationary phase was added into 30 ml of LS suspension medium with 1 mM Colchicine (Sigma, Catalog #C3915) and cultured for 7 days. The single cells were produced from 3-7 days of cultures and are ready for transformation experiments. The single cells of carrot could be maintained at stationary phase up to 28 days by diluting the cultures at 14 days by adding 60 ml of fresh LS BY2 liquid medium.

WHISKERS™ Mediated Genetic Transformation of Carrot Single Cells.

Single cells produced in LSBY2 medium with 1 mM Colchicine were observed at 4 days and at 11 days after culture initiation. The single cells are very active and viable as determined by fluorescein diacetate stain. Yellow fluorescent protein expressing callus events were observed from single cells derived colony, 10 days and 25 days after selection on glufosinate ammonium plates Genetic Transformation Carrot Single Cells.

Modified WHISKERS™ transformation protocol [Petolino, Welter and Cai (2003) Molecular Methods of Plant Analysis, Vol. 23, 147-158, Chater9, Genetic Transformation of Plants, ISBN 3540002928] was used in the transformation experiment. The experiments were initiated by transferring 25 ml of single cell carrot suspension on day 4 days and 11 days after single cell treatment and culture initation into sterile 250 ml IEC-centrifuge bottles (Fisher Scientific catalog #05-433B). Transformations were carried out by adding 8.1 ml of freshly prepared 5% Whiskers Suspension (Silar SC-9, Advanced Composit Materilas Corp, Greer, S.C.) and 170 ug of pDAB3831 containing the AtUbi10 promoter driving the PAT gene and CSVMS promoter driving the YFP gene. Each transformation consisted of one bottle which was placed in the modified paint mixer (Red Devil Equipment Co, Minneapolis, Minn.) and agitated on high for 10 seconds, after which cells were returned to a 500 ml recovery flask and 100 ml of fresh LSBY2 liquid media was added. Cells were allowed to recover for 1 hour on a rotary shaker at 125 rpm and 28° C.

Following recovery, 3 ml aliquots of cell suspension were evenly dispensed on to sterile 55 mm number 4 filter paper discs (Whatman International Ltd.) resting on a Buchner funnel and liquid medium aspirated off. Filter papers with cells were then placed on 60×20 mm Petri dishes containing semi-solid LSBY2-B15 medium with 15 mg/l glufosinate ammonium and 0.8% TC agar as gelling agent. Plates were incubated at 28° C. in the dark. After 10 days, events expressing GFP were pulled off of the filter paper and placed on individual plates of LSBY2-B15 semi-solid. The remaining filter and cells were transferred to fresh semi-solid LSBY2-B15 medium and incubated in the dark at 28° C.

Analyses of the Single Cell Colony Events.

Putative transgenic events that were uniformly fluorescing under a Leica inverted fluorescent scope 25 days after initiation of transformation experiments were analyzed for the functional selectable PAT marker protein through a sensitive ELISA assay using the "EnviroLogix LibertyLink® PAT/pat Plate Kit." The EnviroLogix LibertyLink® PAT/pat Plate Kit is a "sandwich" Enzyme-Linked ImmunoSorbent Assay (ELISA). The callus tissue was placed in a microcentrifuge tube and 250 ul of extraction buffer was added. The extraction buffer was PBS (Fisher Catalog #BP665-1) and 0.05% Tween −20 (Sigma-Aldrich Catalog #P1379). The tissue was ground with a small, hand-held pestle in the microcentrifuge tube. The sample extract was centrifuged at 11,000 ref for one minute, and the supernatant was used in the ELISA at the following dilutions 1:1, 1:2, 1:4, 1:8, 1:16, 1:32, and 1:64. The ELISA methods were followed as stated in the Envirologix kit Catalog number AP014. In the test, the sample extracts are added to test wells coated with antibodies raised against PAT from the pat gene. Any residues present in the sample extract bind to the antibodies, and are then detected by addition of enzyme (horseradish peroxidase) labeled PAT/pat antibody. After a simple wash step, the results of the assay are visualized with a color development step; color development is proportional to PAT/pat concentration in the sample extract.

The result showed that the negative control tissue at a sample ratio of 143 mg/250 ul of extraction buffer did not produce a value in the PAT ELISA. The event 001B at a sample ratio of 63 mg/250 ul did produce an ELISA value of 83 ng/ml, which equals 330 pg of PAT per mg of callus and thus indicating a brightly fluorescing event that is indeed transformed with both PhiYFP fluorescing in the expected range and also with the PAT selectable marker gene.

EXAMPLE 12

Chemical Class of Microtubule Inhibitors and Plant Single Cell Production

The parallelism between microtubules and microfibrils represents a correlated response to an unknown polarizing principle rather than a causal relation (Emons et al., 1992). This is supported by several examples where most cells in the maturation zone of the water-stressed maize (Zea mays) root have microtubule arrays in right-handed helices but microfibrils in left-handed helices (Baskin et al., 1999). Similarly, the Arabidopsis (Arabidopsis thaliana) mutant, microtubule organization 1 (mor1), has aberrant microtubule arrays but apparently unaltered microfibril alignment (Himmelspach et al., 2003; Sugimoto et al., 2003). Single cell suspension in our experiments shows a growth response similar to that of control where the dry weight increases over the cell subculture cycle indicating that the cells divide in the lower concentration of Microtubulin inhibitors (MTIs), despite the fact that they have cells showing the isotropic growth with radial expansion. In addition, by altering medium composition it is possible to see the cell plate in such single cells with isotropic growth photographed which further support the fact that these cells indeed are dividing in low levels of MTI concentration. Thus, plant cells treated with low concentrations of a microtubule inhibitor and maintained in the optimal levels in the medium could have a substantial population of cortical microtubules remain unaltered. This would allow the single cells to carry on with the normal cell wall building process including the phragmoplast building, which is an important pre-requisite for cell division.

To inhibit microtubule function partially and to choose compounds that are selective in disrupting them in low levels, different classes of compounds were screened. MTI interaction with plant tubulin has been well characterized (Hugdahl and Morejohn, 1993). Nevertheless, with any inhibitor, there are nonspecific effects (Vaughn and Lehnen, 1991). Therefore, in this example a comparison of Microtubule inhibitors class with different chemistry was evaluated to identify compounds that could sustain the growth of single cells without nonspecific effects. There are compounds such as clorpropham, known to inhibited elongation at lower concentrations than needed to stimulate radial expansion, as they affected mitotic microtubules more actively than cortical ones (Hoffman and Vaughn, 1994). Thus, an objective of this work was to select compounds that in low optimal concentration would retain sufficient cortical microtubules to carry out the normal cellular function while maintaining the isotropic growth, but at the same time with low or now nonspecific inhibitory effect.

Colchicine is a tropolone derivative, the stereochemical structure and the mode of action of which are well-established (Keats and Mason, 1981; Margolis and Wilson, 1977; Raugh and Wilson, 1980), Murgulis, 1974), and it prevents the formation of microtubules from tubulin dimers. Propyzamide and the other benzamide act on the nuclear spindle in plant cells (Akashi et. al., 1988; Bartels P G and Hilton J L., 1973; Carlson et. al., 1975) and were developed as preemergence herbicides that are effective on annual grasses and broadleaf weeds (Aya et. al., 1975). The uses of phosphoric amides are similar to those of the dinitroaniline herbicides including oryzalin (Surflan) and trifluralin (Treflan) (Ashton and Crafts, 1981). Trifluralin is one of the best-known representatives of the dinitroaniline herbicide family; it destroys plant microtubules but is ineffective in animal cells (Hess and Bayer, 1974; Hess and Bayer, 1977). Pyridines have a benzene ring with one of the carbons replaced by a nitrogen. There are several substituted pyridines used as herbicides. In this group are dithiopyr (Dimension®) and thiazopyr (Visor®). Dithiopyr is a selective pre- and postemergence material, used only on turf to control a wide variety of grass weeds. It is frequently formulated with other herbicides and on fertilizers. Thiazopyr is a selective pre-emergence compound that works well for practically all grass weeds, and on a wide variety of crops, including citrus, cotton, corn, peanuts, soybeans and potatoes. Thus, pyridines appear to be microtubule assembly inhibitors in function.

Materials and Methods

JTNT1 Tobacco Suspension Cultures. The JTNT1 tobacco cell suspension cultures were maintained by subculturing 1 ml of packed cell volume (PCV) into 20 ml of tobacco media (MS salts, myo-inositol, Thiamine HCl (1 mg/ml), Potassium Phosphate Dibasic (anhydrous), MES, 2,4-D (10 mg/ml) and 3% glycerol (NT1B medium). The cell line was sub-cultured every 7 days, and bulked as needed for testing. 1 M sucrose inhibited both the rate and extent of taxol induced plant tubulin polymerization (Bokros et al., 1993). Investigation of plant tubulin polymerization in the presence of 1 M Sucrose (both APM, Amiprophosmethyl, and oryzalin) produced a concentration-dependent decrease in plant microtubule length (Morejohn and Fosket, 1984; Morejohn et al., 1987). Furthermore, Sue stabilizes preformed microtubules, making an examination of the effects of MTIs on preformed microtubules unfeasible. In addition, sucrose increases solution viscosity substantially, and tubulin polymerization is altered at least in part by slowed dimer and polymer diffusion rates. Thus, it was important to have low or no sucrose in medium where the single cell production. Thus, a new JTNT1 line habituated in Glycerol was developed for this study.

For treatments, the suspension lines were prepared with 1 ml PCV in 20 ml of medium, while swirling frequently to allow good cell distribution (as the suspension aggregates tend to sediment) and then transferred into the wells of 24-well micro-titer plates. Each of the 24 well contained 1 ml of JTNT1 suspension. The 24-well plates were kept on an Innova 4900 Multi Environmental Shaker with special clamps and harnesses to allow stacking of plates up to 6 plates high. The plates were rotated at a speed of 130 rpm and 25° C. in dark.

Single Cell Production. Each compound was dissolved in dimethyl sulfoxide (DMSO) to provide 0.5 Molar stock solutions. One ml of JTNT1 suspension (1 ml PCV/20 ml tobacco media) was added to each well of the 24 well plates. To each well an individual chemical was added to achieve the desired concentrations (at 1 µM, 3 µM, and 10 µM). The cultures were allowed to grow for 7 days on the Innova Shaker. Each day turbidity measurements was taken on each well using a SpectraMax M2$^e$ by Molecular devices (set at 600 absorbance, with 5 readings taken per well). On day 7, cells were observed using the Leica 5000 inverted confocal microscope for formation of single cells and cell viability.

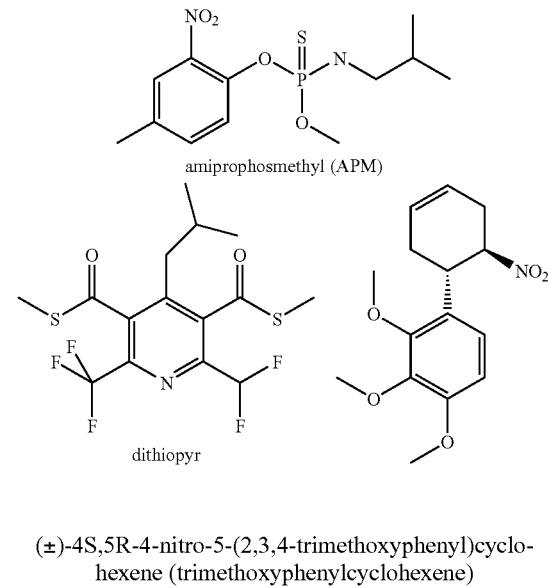

amiprophosmethyl (APM)

dithiopyr (±)-4S,5R-4-nitro-5-(2,3,4-trimethoxyphenyl)cyclohexene (trimethoxyphenylcyclohexene)

Clonal callus event production through BY2 single cells in LSBY2 glycerol medium. Tobacco BY-2 cells (Nagata et al., 1992) were transformed by pDAB1590 via a modified protocol described by Shaul et.al., 1996 and selected on the LSBY15 after 4 days of co-cultivation. The green fluorescent protein expressing callus event was recovered, and the callus was maintained on LSBY2 B15 medium. Within a month, a callus event grew to several centimeters in diameter, and a small but brightly fluorescing piece (~2 to 5 mm2 clump) was transferred to fresh solid medium to keep the cells supplied with nutrients in fresh selection agent and to select homogenously GFP expressing callus. A 500 mg piece of callus was transferred to a 50 ml of LSBY2-Gly-B15, a modified LSBY2 liquid medium with 3% glycerol and 1% sucrose as carbon source in a 250 ml shake flask (130 rpm at 25° C. in dark). Every week a 0.5 ml Pack Cell Volume (PCV) of cells were used to start a suspension culture. Thus green fluorescent protein (GFP) expressing callus and suspension aggregates were maintained in a monthly and 7 day cycle respectively.

Production of GFP expressing single cells. Single cells were produced by adding 1 uM concentration of the compound DDP (diphenylpyrazole) during the initiation of the 7d culture cycle in the LSBY2-Gly-B15 medium along with the addition of 0.5 ml Pack Cell Volume (PCV) of GFP expressing suspension aggregates at the stationary phase. Alternately, a 25-ml of suspension aggregates were transferred to a 25-ml of fresh LSBY2-Gly-B15 suspension medium by adding 50 ul of 1M diphenylpyrazole stock solution dissolved in DMSO to provide a 1 uM final concentration in the suspension. Thus single cells could be produced in a much shorter cycle of only 3.5 days. The LSBY215 medium always contain 15 mg/l glufosinate ammonium for selection GFP was expressed as a chimeric protein in single cells through out the 3.5 or 7d culture cycles and were resident in subcellular locations as the GFP expression of the chimeric constructs was observed in living cells using conventional epifluorescence using a Leica Microscope and also using a Zeiss Axiovision confocal laser scanning microscopes. The expression was seen in many of the subcellular compartments including the nucleus and the cytoplasmic strands Results and Discussion.

The cells were very healthy in the tobacco culture media containing glycerol and the cell clusters were very evident.

The cells showed good biomass increase over a period of 7 days though there was ~50% reduction in the biomass compared to control with sugar. The control cultures also had 0.1% DMSO to make sure that there is no DMSO induced effect. Addition of 1 uM 4-Chlor-1,5-diphenyl-1H-pyrazol-3-yloxy)-acetic acid ethyl ester (diphenylpyrazole) to either sucrose or glycerol medium did not reduce the biomass of the cells significantly from the respective controls indicating that there is active growth of single cells similar to the control in the presence of diphenylpyrazole. The growth curvature is similar when the cultures were taken through 2 subcycle or 3.5 days. The single cell production in glycerol medium also shows very high viable cells compared to control.

Several other compounds including Trifluralin, Oryzalin, and Microtubulin stabilizer class compounds such as Taxol have been studied for their efficiency of producing single cells from Tobacco JTNT1 suspension culture cultured in NT1B medium with 3% glycerol as the sole carbon source. These were colchicine, N-(1,1-dimethylpropynyl)-3-chlorobenzamide, propyzamide and trifluralin. In these studies, the compounds differed in their single cell production efficiencies and in the steepness of the dose-response curve. Oryzalin, like the other compounds tested, increased diameter of single cells at least 4-fold and had a saturating concentration about 10 times the threshold. Colchicine increased diameter 5-fold and had a steeper dose-response curve, which indicates that these two compounds may be preferable for work at high doses.

The concentrations necessary to produce single cells were in the range of 50 uM and 2 mM for colchicine, and between 10 nM and 100 uM for propyzamide, N-(1,1-dimethylpropynyl)-3-chlorobenzamide. However, the concentrations of Oryzalin and Trifluarlin for optimal single cell production ranged from 100 nM to 1 mM. However, in high concentrations of these compounds increased protein synthesis, plastid and mitochondrion division occurred in the treated cells, leading to the formation of giant cells of up to 300 uM in diameter with nuclear polyploidy as seen in carrot cells cultured for 21 days. These results suggest that mitosis inhibition is the fundamental effect of these compounds at high concentrations studied. Thus, it appeared important to keep not only the optimum concentration of MTIs, but also the chemistry of the compound (which will have very selective function on the tubules and not the nonselective function similar to the cell division function). In line with an objective, other compounds are described below besides diphenylpyrazole described earlier.

BY2 suspension aggregates were observed: in LSBY2 sugar medium; dividing BY2 single cell produced in 1 uM diphenylpyrazole showing the cell plate in a modified LSBY2 medium; BY2 GFP transgenic cells deconvoluted and single clonal colony event on the LSBY2-15 gel medium.

Summary of Tobacco BY2 Single cell production in LSBY2 Glycerol medium. Single cells produced in 1 uM diphenylpyrazole from aggregates suspension shows single nucleus with one or two nucleoli in 90% of the cells on 3.5 days of culture. These cells could be plated on a LSBY2 gel plate with 0.8% TC agar and 15 mg/l glfosinate ammonium as the selection agent since the pDAB 1590 plasmid used to transform the aggregates suspension had PAT as a selectable marker. The cells were diluted in the liquid medium in a 1:4 dilution and plated on the gel medium and selected clonal event in 21 days after plating.

Regarding Amiprophosmethyl (APM) when added to the JTNT1 suspensions, single cells were formed in the 1-10 μM concentration; at higher concentration there is remarkable reduction of growth and cell division inhibition. Round separate cells can be seen in pictures of 1 μM and 3 μM APM compared to the control with only DMSO. The JTNT1 tobacco cells were a healthy yellow color and grew well in the presence of 1 μM and 3 μM APM. The cell viability, as measured by Fluorescein diacetate and Propidium Iodine stains, showed viability up to 70%.

Again, APM induced single cell production of JTNT1 tobacco cells in Glycerol medium was observed. JTNT1 control suspension aggregate was observed in medium with glycerol and 0.1% DMSO; JTNT1 single cells were observed in NT1B glycerol media with 1, 3, and 10 uM APM.

Dithiopyr belongs to the class of substituted pyridine herbicide which disrupt microtubule. When added to the JTNT1 suspensions at concentrations of 1 μM, 3 μM, and 10 μM, single cells were formed using 1 μM and 3 μM concentrations (pictures E and F), but the 10 μM concentration had single cells (and the concentration of the cells was low). The tobacco cells were healthy, growing and yellow in color using the dithiopyr in all concentration tested. Cell viability after treatment with 1 μM and 3 μM dithiopyr was between 70-80%, indicating a higher viability.

A colchicine mimetic (Evans et al., 2003), (±)-4S,5R-4-nitro-5-(2,3,4-trimethoxyphenyl)-cyclohexene (trimethoxyphenylcyclohexene), was tested in the JTNT1 tobacco cultures for its single cell production efficiency. While there was a mild bleaching in the cells (they were a slightly duller yellow), the cells grew very well on the plate. This chemical promoted the formation of single cells at 1 μM, 3 μM, and 10 μM. The cells were round and cell viability across all levels ranged from 80-90%. Cell growth inhibition is rather similar among the concentration tested and the cells were healthy with high viability and less of cytotoxicity.

Thus, induced single cell production of JTNT1 tobacco cells was observed in Glycerol medium induced in 10 uM concentration of trimethoxyphenylcyclohexene.

Super single cells. Carrot suspension aggregates could be cultured in 1 mM colchicine in 60 ml of LSBY2 liquid medium and maintained in the same medium for up to 28 days. The growth after the second subculture declines after 14 days, but the cells keep growing to form super single cells that are alive and healthy (but showing extensive lobed nuclei indicating the occurrence of nuclear polyploidy). Carrot super single cells with several nuclei were observed in 21 d old cells with continuous 1 mM colchicine in LSBY2 medium Conclusion. The cell growth in these tests levels were observed by visual observation, dry weight (taken at day 7 only), and turbidity readings. FIG. 15 depicted turbidity readings taken in a 7 day period. Turbidity readings were relative to plates containing only the media (with 3% glycerol) and the microtubule inhibitor at 1 μM, 3 μM, and 10 μM concentrations. While the controls have the best growth patterns, as expected, none of the chemicals tested cause the cell lines to die at rates of 1 μM and 3 μM. Cells in all of the treatments experienced an increase in growth rate around the same time point (day 3), and the cell volume was still increasing at day 7. This shows chemically treated cells remained viable for at least 7 days.

EXAMPLE 12

References

1. Akashi et.al., (1988). Plant Cell Physiol 29(6):1053-1062
2. Aya, et. al., (1975). Fifth Asian-Pacific Weed Science Society Conference, pp 138-141

3. Bartels P G and Hilton J L (1973). Pestic Biochem Physiol 3: 462-472
4. Carlson et. al., (1975). Weed Sci 23: 155-161
5. Emons et. al., (1992) Physiol Plant 84: 486-493
6. Evans et. al., (2003). *Tetrahedron,* 59, 2223-2229),
7. Hess F D and Bayer D E (1974). Acala 4-42") J Cell Sci 15:429-441
8. Hess F D and Bayer D E (1977). J Cell Sci 24: 351-360
9. Himmelspach et. al., (2003). Plant J 36: 565-575
10. Hoffman J C, Vaughn K C (1994). Protoplasma 179: 16-25
11. Hugdahl J D, Morejohn L C (1993) Plant Physiol 102: 725-740
12. Keates R A B and Mason G B (1981). Can J Biochem 59:361-370
13. Margolis R L and Wilson L (1977). Proc Natl Acad Sci USA 74: 3466-3470
14. Murthy, J., et al., (1994). *Plant Physiology* 105, 309-320).
15. Margulis T N (1974). J Am Chem Soc 96: 899-901
16. Nagata, T., Nemoto, Y. & Hasezawa, S. (1992) Int. Rev. Cytol. 132, 1-30.
17. Rauch C T and Wilson L (1980). Biochemistry 19: 5550-5557
18. Shaul O, Mironov V, Burssens S, Van Montagu M, Inzé D (1996). Proc Natl Acad Sci USA 93: 4868-4872
19. Sugimoto K, et.al., (2003) Plant Cell 15: 1414-1429
20. Vaughn, K., (2006). *Pesticide Biochemistry and Physiology,* vol 84(2), 63-71)
21. Vaughn K C, Lehnen L P Jr (1991). Weed Sci 39: 450-457

EXAMPLE 13

A Comparative Investigation on MTI Produced Single Cell Sub-Cellular Structure, Cytogenesis, and Molecular Genomic Instability Assessment Gross genome stability in tissue culture derived plants has been studied at the cytogenetic level in several plant species (Shoyama et al. 1995; Zoriniants et. al. 2003). Regarding stability of embling derived plants, cytogenetic studies have revealed contrasting observations. Odake et. al. (1993) reported chromosome doubling (from diploid to tetraploid) in 66.7% and 100% emblings of *Asparagus officinalis* L. obtained from Gellan Gum-solidified medium and liquid medium, respectively. In contrast, Mamiya et. al. (2001) reported no ploidy changes during somatic embryogenesis in *A. officinalis*. Synthetic auxins, such as 2,4-D (2,4-dichlorophenoxyacetic acid) and NAA (naphthalene acetic acid), used in culture media have been reported to be associated with somaclonal variation (Karp 1989; Phillips et. al. 1994). Indeed, a reduction in ploidy was reported in both carrot (Ronchi et al. 1992) and poplar (Rugh et. al. 1993) somatic embryogenesis systems in which 2,4-D had been used. Microtubulin inhibitors (MTI) also increase ploidy in plant cells. However, the concentration and the MTI compound class determine the nature of ploidy or the absence of ploidy. For example, Oryzalin induces nuclear polyploidy in TBY2 cells, but not propazamide at similar concentrations (Ehsan et. al., 1999). Similarly, long term exposure of carrot suspension cells induces nuclear polyploidy in higher concentration of colchicine. Carrot suspension cells showed nuclear polyploidy in 1 mM colchicines cultured single cells from 14-21 days of continuous treatments. However, the frequency of such ploidy levels is much less in cultures up to 14 days and less <1% which is similar to control reported for auxin cultured controls suspensions ((Karp 1989; Phillips et al. 1994). However, among compounds tested in this study 4-Chlor-1,5-dipenyl-1H-pyrazol-3-yloxy)-acetic acid ethyl ester and 4S,5R-4-nitro-5-(2,3,4-trimethoxyphenyl)cyclohexene showed efficient single cell production with low or no nuclear ploidy percentage in 14 days of continuous treatments.

In any case, the single cell induction process from cell aggregates using such low cytotoxic MTI could still alter the existing gene expression patterns of single cells with a different gene expression profile. DNA methylation is well known to trigger undesirable consequences leading to somaclonal variation in vitro. In addition, MTI induce changes that could result in molecular variation or instabilities. A polymorphic percentage of 1.09% was reported in colchicine induced chromosome doubling in tetraploids of *Eragrostis curvula* (Mecchia et. al. 2007). The concentration level of colchicine used to treat the *E. curvula* seeds is 0.05%. An objective of the present study was to evaluate the genomic stability in JTNT1 single cells produced in 1 uM 4-Chlor-1,5-dipenyl-1H-pyrazol-3-yloxy)-acetic acid ethyl ester.

Various molecular approaches such as AFLP, RAPD (rapid amplified polymorphic DNA), RFLP (restriction fragment length polymorphism) have been attempted to identify and measure the level of somaclonal variation in tissue culture derived plants (Devarumath et. al. 2002; Martins et. al. 2004; Sanchez-Teyer et. al. 2003; Hale and Miller 2005). Irrespective of the methodology used, however, only a very small percentage (much less than 1%) of the genome can be assayed however prolific the technique (in terms of number of loci sampled). Of the various techniques available, AFLP is the most highly multiplex with typically 50-100 loci assayed per primer pair. These loci are thought to be scattered more or less randomly throughout the genome and thus AFLPs offer the best chance for detecting tissue culture-induced changes. Moreover, AFLP is also one of the more robust molecular techniques for cultivar identification and variability analysis (Hale and Miller 2005). Thus, this method of evaluation was chosen for use in this study.

Materials and Methods.

JTNT1 Tobacco single cell initiation and sample collection. JTNT1 Tobacco single cells were initiated in two different media, NT1B with 3% sucrose (NT1B-Suc) and NT1B with 3% glycerol (NT1B-Gly) in 3.5 day culture cycle. The cultures were started by adding 12.5-ml suspension aggregates at stationary phase cultures maintained in respective culture medium and transferred to 12.5-ml fresh culture medium in a 125-ml shake flasks containing 1 uM 4-Chlor-1,5-diphenyl-1H-pyrazol-3-yloxy)-acetic acid ethyl ester (diphenylpyrazole). The flasks were closed with a foam stopper and cultured on a orbital shaker at 130 rpm in dark at 25-28° C. The cultures were sub cultured every 3.5 days up to a period of 14 days. Four samples (Suc/Gly grown cells and the control cultures in Suc/Gly media with 0.2% DMSO) of the cultures were harvested at every 3.5d by spinning the suspension at 3000 rpm for 5 minutes. The samples were immediately lyophilized to prevent any cell oxidation to minimize any deleterious effect on the samples introduced post harvest. Single cells were stained with Hoechst nuclear stain for an hour and observed under scopes for any nuclear anomaly up to two culture cycles.

Cytological Characterization of Single Cells.

Cell viability and Cell wall. Established JTNT1 single cells were used to stain with FUN1 (F-7030,Molecular Probes, Invitrogen Inc) cell stain which is used for viability test in yeast, and this contains two color fluorescent probes. The third one, Calcofluor White M2R which stains cell wall, was used to stain the cells. For JTNT1 single cells, 20 μm of FUN1 stain is added and the culture was incubated at room temperature for 20 mins. 1 mL fresh culture media was added to wash the excess stain and centrifuged at 3000 rpm; the supernantant was discareded. The cells were examined and imaged on Zeiss ApoTome microscope.

Plasmamembrane. JTNT1 cells were incubated with 5 μm FM4-64 (styryl dye) for 5 minutes and washed with fresh media. The culture was centrifuged at 3000 rpm, and fresh media was added. The cells were visualized on Zeiss Apo-Tome microscope.

Nucleus. Single cells were stained with Hoechst nuclear stain for an hour and observed on Zeiss Apo Tome for any nuclear anomaly up to two culture cycles. Crystal violet stain was also used as a live nuclear stain for observing nuclear structure for ploidy characterization Cytoskeleton. Phallotoxins bind to actin filaments. Alex Fluor 488 Phalloidin (A12379 Invtrogen Inc) was used to stain single cells. 6.6 um of Alex fluor was added to the single cells and incubated for 30 minutes and imaged on the microscope.

Molecular Assessment for Genomic Instability.

DNA extraction. Genomic DNA from representative samples were harvested from 3.5, 7, 10.5, and 14 days. Suc and Gly cultures along with the controls (10 samples) were extracted using CTAB protocol (See Appendix—Example 12). DNA was quantified using PicoGreen® dye from Molecular Probes, Inc. (Eugene, Oreg.). Each well of a microtiter plate contained 90 μl of 200-fold picogreen combined with 10 μl of DNA sample at 40× dilution or Lambda DNA standards (0, 2.5, 5 and 10 ng/μl). Plates were shaken briefly using standard plate shaker, and fluorescence was read (excitation ~480 nm, emission ~520 nm) using Spectra Max GeminiXS fluorometer from Molecular Devices (Sunnyvale, Calif.). Each sample was quantified in triplicate, and an average of the three results was used for subsequent dilutions. The DNA sample concentrations were diluted to working concentration of 91 ng/μd with sterile water.

AFLP analysis. Amplified fragment length polymorphism (AFLP) assays were performed using a modification of the protocol of Vos et. al. (1995), as described in Bryan et. al. (2002). The 6-bp cutting restriction enzyme EcoRI was used in combination with the 4-bp cutting restriction enzyme MseI. EcoR1 fluorescently labeled and Mse1 non-labeled AFLP primers were ordered from Applied Biosystems (Foster City, Calif.). AFLP analysis was carried out using Applied Biosystems' AFLP Plant Mapping Protocol through the selective amplification reaction with one modification. The modification was that digestion/ligation reactions were incubated at 37° C. overnight. Selectively amplified products were diluted 2 fold in sterilized deionized water. 0.5 ul of the diluted product was combined with 5 ul of loading buffer (5 ul GeneScan 500 by LIZ size standard mixed with 500 ul ABI HiDi Formamide). Samples were analyzed on an AB3730XL DNA Analyzer with G5-RCT spectral matrix using standard conditions. Data was then imported into GeneMapper® version 4.0 (Applied Biosystems, 2005). Alleles were assigned a numeric value according to PCR fragment size.

Results and Discussion.

Cytology and Other Sub-Cellular Assessment of Single Cells.

Cell wall and cell division. During cell culture, growth and differentiation occurs, and the shape and structure of the cells rely upon the cell wall. Single cells showed isotropic growth with a 3-10 fold increase in size showing a typical circular cell. In order to understand the cell wall structure, calcofluor (a whitening agent which has binding affinity to celluloses) was used. In the single cells, a distinct circular wall was observed. The cell wall is a dynamic structure which plays an important role in determining cell shape and interacts with environmental factors. Though most of single cells observed showed a spherical cell, it was possible to see dividing cells with wall plate. The gaining of dry weight is another indication that there is cell division occurring in these single cells. After 14 days of culture in MTI, if the single cells are transferred to MTI free medium the cells reconstituted the aggregate suspension showing the reversibility of the anisotropic growth.

Plasma membrane. Plasma membrane is one of the important components of cell which encloses all cell contents. It outlines the cell wall and provides the final filter between the cell interior and the environment. Amphiphilic FM styryl dyes are useful to study organelle organization and vesicle trafficking in living eukaryotic cells (Bolte et. al., 2004). Initially the FM dyes localize to plasma membrane (PM) then endocytosed in to vacuole and vesicle then in to endosomes. FM4-64 (a membrane selective fluorescent dye) stains the plasma membrane and then internalizes to other organelles in the cells (Ueda et. al., 2001). After 5 minutes of staining, the single cells fluorescence was observed on the plasma membrane, and there are no structural defects. In single samples where 100 nM Isoxeben is used to remove the cellulose network, the FM4-64 showed extensive vesicle on the surface. The membrane showed active endocytosis within 5 minutes Nucleus. Nuclear organization in MTI treated plant cell is reported to be complex and nuclear polyploidy is shown to be common in higher concentrations. The samples were examined up to 7 days in 1 uM concentrations of diphenylpyrazole and trimethoxyphenylcyclohexene. Nuclear organellar structure was analyzed by using various stains (Hoechst3325). In JTNT1, single cells contain a single nucleus with one nucleus or two nucleoli in 1 uM concentrations of diphenylpyrazole and trimethoxyphenylcyclohexene in 3.5d cultures. However, high concentrations of these compounds lead to the formation of giant cells of up to 150-300 uM in diameter with nuclear polyploidy as seen in carrot cells cultured for 21 days. These results suggest that mitosis inhibition is the fundamental effect of these compounds at high concentrations studied. Thus, it is important to keep not only the optimum concentration of MTIs, but also the chemistry of the compound, which will have very selective function on the tubules and not the nonselective function similar to the cell division function.

Cytoskeleton. Cytoskeleton consists of several structural proteins such as F-actins and tubulins which are involved in the structural integrity of cell structure. Cytoskeleton in vivo dynamics were studied using Green Fluorescent Alexa flour 488 actin conjugate (Al2373) which is brighter and less pH dependent. Micro tubules and actin filaments are essential structures for maintenance of cytoskeleton structure in plant cells for their growth and differentiation and survival of plant cells(Kost et. al., 2002). The single cells stained with phalloidin showed the actin filament cytoskeleton, and there were no defective positioning of the filaments as the cell structure is normal.

Molecular analysis. The AFLP analysis involved 10 primer combinations based on the use of EcoRI (a methylation insensitive restriction enzyme). Two of the primer pairs failed to amplify (p6, and p10) and two of the primer pairs showed no differences on any of the fragments (3p and 8p). The number of clearly separated fragments for the primer pairs 1p, 2p, 3p, 4p, 5p, 7p, 8p, 9p was 47, 39, 31, 42, 47, 32, 7, and 46, respectively. No AFLP polymorphism was detected among all the samples treated with the methylation insensitive (i.e. EcoRI-MseI) primer combinations except the 14 day glycerol cultured samples of JTNT1 ($4^{th}$ subculture cycle). In contrast, no polymorphic fragments were identified in all the other samples for glycerol cultured samples. The sucrose treated samples showed no polymorphisms for any of the fragments for any of the primer combinations tested. As expected, there were no differences in the single cell samples for at least 3 subculture cycles. However, the 4 sub-culture cycle the polymorphism in Glycerol cultures may be due to the continuous presence of the compound in addition to the stress imposed by the lack of sucrose (which seems to have triggered the instability). The difference in the JTNT1 single cell culture showing no polymorphism suggest that the simple carbon source glycerol, though known to stabilize the microtubules, may not be able to support a lot of cellular function especially in the prolonged presence of a Microtubulin inhibitor (MTI). In any case, single cell treatments could be successfully prepared in the concentration range tested with diphenylpyrazole for at least 4 subculture cycles with out genomic instability problem.

Snapshots of 2 polymorphism for primer 5p were taken. Sub-culture 4 had a 130 by fragment insertion and a 131 by fragment deletion.

AFLP profiles involving the use of methylation insensitive enzymes EcoRI and MseI with primer-pair combination were determined. All samples for 4 sub-culture cycle were monomorphic, while profile of Glycerol at $4^{th}$ sub-culture cycle was polymorphic at various loci.

culture regenerants of pea (Cecchini et. al. 1992). Thus, to further evaluate methylation based variation, further evaluation with the methylation sensitive PStI/MseI combination can be conducted.

APPENDIX-EXAMPLE 13

CTAB DNA Extraction from Tobacco Cell Suspension/Callus Tissues

1. Weigh out ~25 mg of lyophilized tissue into a 2 ml Eppendorf tube.
2. Place stainless steel bead into tube with tissue and shake on geno-grinder or paint shaker for approx 1 minute. (Geno-grinder set at 500 strokes/min) Remove bead and gently tap tube to reduce tissue clumping.
3. Add 1 ml extraction buffer and gently tap tube to reduce tissue clumping and get tissue into buffer, incubate while gently mixing on their sides for 2 hours at 65° C. Cool to room temperature (~10 minutes).
   Extraction Buffer (250 mls)
   Tris-HCl 25 mls
   NaCl 29.2 g
   Na EDTA 12.5 mls
   CTAB 6.25 g
   PVP 3.75 g
   Water (add up to final volume of 250 mls)

TABLE 2

Provides details of AFLP primer combinations used and the corresponding numbers of bands observed. Suc-X, Single cells in NT1B-Sucrose medium; Gly-X, Single cells in NT1B-Glycerol medium; Cont-Suc, Control JTNT1 suspension aggreagates in sucrose; Cont-Gly, Control JTNT1 suspension aggreagates in Glycerol

| Primer comb. | Primer sequence (5' to 3') | Cont Suc | Cont Gly | 3.5 d Suc | 3.5 d Gly | 7 d Suc | 7 d Gly | 10.5 d Suc | 10.5 d Gly | 14 d Suc | 14 d Gly |
|---|---|---|---|---|---|---|---|---|---|---|---|
| EcoRI/MseI combination | | | | | | | | | | | |
| 1p | AC/CAG | n/a | n/a | 0 | 0 | 0 | 0 | 0 | 0 | 0 | 5 |
| 2p | AGC/CAG | n/a | n/a | 0 | 0 | 0 | 0 | 0 | 0 | 0 | 10 |
| 3p | AGC/CTG | n/a | n/a | 0 | 0 | 0 | 0 | 0 | 0 | 0 | 0 |
| 4p | ACT/CTT | n/a | n/a | 0 | 0 | 0 | 0 | 0 | 0 | 0 | 5 |
| 5p | ACT/GAG | n/a | n/a | 0 | 0 | 0 | 0 | 0 | 0 | 0 | 3 |
| 6p | ACT/CTG | n/a | n/a | | | | | | | | |
| 7p | ACC/CAG | n/a | n/a | 0 | 0 | 0 | 0 | 0 | 0 | 0 | 4 |
| 8p | ACC/CTG | n/a | n/a | 0 | 0 | 0 | 0 | 0 | 0 | 0 | 0 |
| 9p | ACA/CAG | n/a | n/a | 0 | 0 | 0 | 0 | 0 | 0 | 0 | 7 |
| 10p | ACA/CTG | n/a | n/a | | | | | | | | |
| Total | | | | | | | | | | | 34 |

Molecular genetic assessment of uniformity. AFLP polymorphism (amongst 4th sub-cultured cycle of Glycerol grown single cell suspension for 9 primer combination out of the primer combination used) were seen in this study. All of the observed variability pertains to fragments generated using EcoRI/MseI. An increase in the methylation status during tissue culture has been reported previously for tomato callus, as compared to leaves (Smulders et. al. 1995) and tissue 4. Add 0.75 ml of 25:24:1 Pheno/Chloroform/Isoamyl Alcohol pH 8 to the extraction buffer and rock gently by hand for 5 min. Centrifuge for 5 minutes at 10,000 rpm to separate phases. Carefully transfer aqueous phase into new tube.
5. Repeat step 4 using 24:1 Chloroform/Octanol instead of Phenol/Chloroform/Isoamyl Alcohol mixture.
6. Add isopropanol to the supernatant in equal volume and let sit for 1 hour at room temperature.

7. Centrifuge tubes for 10 minutes at 10,000 rpm and pour off supernatant being careful to keep pellet in bottom of tube.
8. Add 0.5 ml of 70% Ethanol and RNase mixture to wash DNA pellet and centrifuge 1 min at 10,000 rpm. (1:1000 Rnase/Ethanol).
9. Carefully pour off supernatant and repeat with a 70% Ethanol only wash. Completely dry pellet by letting sit at room temp for 3 hours or rotovap samples for ~5 minutes.
10. Once no droplets of alcohol are present, dissolve pellet in 0.2 ml 1× Tris EDTA buffer that has been pre-warmed to 65° C. Let samples sit over night at room temperature to fully resuspend.
11. Next morning gently rock tubes to mix. Run samples on agarose gel to check for degradation and the presence of RNA and quantify.

EXAMPLE 13

References

1. Mecchia, M. A., A. Ochogavia, J. P. Selva, N. Laspina, S. Felitti, L. G. Martelotto, G. Spangenberg, V. Echenique, S. C. Pessino, (2007). Genome polymorphisms and gene differential expression in a 'back-and-forth' ploidy-altered series of weeping lovegrass (*Eragrostis curvula*), J. Plant Physiol., 164: 1051-1061.
2. Bryan G J, McLean K, Bradshaw J E, Phillips M, Castelli L, De Jong W S, Waugh R (2002) Mapping QTL for resistance to the cyst nematode *Globodera pallida* derived from the wild potato species *Solanum vernei*. Theor Appl Genet. 105:68-77.
3. Devarumath R M, Nandy S, Rani V, Marimuthu S, Muraleedharan N, Raina S N (2002) RAPD, ISSR and RFLP fingerprints as useful markers to evaluate genetic integrity of micropropagated plants of three diploid and triploid elite tea clones representing *Camellia sinensis* (China type) and *C. assamica* ssp. *assamica* (Assam-India type). Plant Cell Rep 21:166-173.
4. Ehsan, H., Luc Roefa, Erwin Wittersa, Jean-Philippe Reichheldb, Dirk Van Bockstaelec, Dirk Inzeb and Harry Van Onckelena (1999). Indomethacin-induced G1/S phase arrest of the plant cell cycle. FEBS Letters, Volume 458, Issue 3, Pages 349-353.
5. Hale A L, Miller J C (2005) Suitability of AFLP and microsatellite marker analysis for discriminating intraclonal variants of the potato cultivar Russet Norkotah. J Am Soc Hortic Sci 130:624-630
6. Karp A (1989) Can genetic instability be controlled in plant tissue cultures? Int Assoc Plant Tiss Cult Newsl 58:2-11.
7. Mamiya K, Sakamoto Y, Ohnishi N, Hirosawa T (2001) Synthetic seeds of *Asparagus officinalis* L. In: Bhojwani S S, Soh W-Y (eds) Current trends in the embryology of angiosperms. Kluwer, Dordrecht, pp 337-352.
8. Martins M, Sarmento D, Oliveira M M (2004) Genetic stability of micropropagated almond plantlets, as assessed by RAPD and ISSR markers. Plant Cell Rep 23:492-496.
9. Odake Y, Udagawa A, Saga H, Mii M (1993) Somatic embryogenesis of tetraploid plants from internodal segments of a diploid cultivar of *Asparagus officinalis* L. grown in liquid culture. Plant Sci 94:173-177.
10. Payne R W, Lane P W, Digby P G N, Harding S A, Leech P K, Morgan G W, Todd A D, Thompson R, Tunnicliffe Wilson G, Welham S J, White R P (1993) Genstat 5 Release 3: reference manual. Oxford University Press, Oxford.
11. Phillips R L, Kaeppler S M, Olhoft P (1994) Genetic instability of plant tissue cultures—breakdown of normal controls. Proc Natl Acad Sci USA 91:5222-5226.
12. Ronchi V N, Giorgetti L, Tonelli M, Martini G (1992) Ploidy reduction and genome segregation in cultured carrot cell lines. 1. Prophase chromosome reduction. Plant Cell Tiss Org 30:107-114.
13. Rugh C L, Parrott W A, Merkle S A (1993) Ploidy variation in embryogenic yellow poplar. In: Proceedings of 22nd Southern Forest Tree Improvement Conference, pp 493.
14. Sanchez-Teyer L F, Quiroz-Figueroa F, Loyola-Vargas V, Infante D (2003) Culture induced variation in plants of *Coffea arabica* cv. *Caturra rojo*, regenerated by direct and indirect somatic embryogenesis. Mol Biotechnol 23:107-115.
15. Shoyama Y, Matsushita H, Zhu X X, Kishira H (1995) Somatic embryogenesis in ginseng (*Panax* species). In: Bajaj YPS (ed) Biotechnology in agriculture and forestry. Springer, Berlin, pp 344-356.
16. Smulders M J M, Rus-Kortekaas W, Vosman B (1995) Tissue culture induced DNA methylation polymorphisms in repetitive DNA of tomato calli and regenerated plants. Theor Appl Genet. 91:1257-1264.
17. Vos P, Hogers R, Bleeker M, Reijans M, Vandelee T, Homes M, Frijters A, Pot J, Peleman J, Kuiper M, Zabeau M (1995) AFLP—a new technique for DNA fingerprinting. Nucleic Acids Res 23:4407-4414.
18. Zoriniants S E, Nosov A V, Monforte-Gonzalez M, Mendes-Zeel M, Loyola-Vargas V M (2003) Variation of nuclear DNA content during somatic embryogenesis and plant regeneration of *Coffea arabica* L. using cytophotometry. Plant Sci 164:141-146.

EXAMPLE 14

Plastid Transformation of Tobacco BY2 Single Cells

Initiation of single cells in preparation for plastid transformation.

Four milliliters of Tobacco BY2 suspension (at the stationary phase growth maintained on a 7-d cycle) was added to 26 mL of fresh medium that composed of either Medium A [LS salts (PhytoTechnology Laboratories, L689), 120 g/L sucrose, 1 mg/L nicotinic acid, 1 mg/L pyridoxine HO, 10 mg/L thiamine HCl, and 20 nM diphenylpyrazole (DPP)] or Medium B [LS salts, 120 g/L sucrose, 1 mg/L nicotinic acid, 1 mg/L pyridoxine HCl, 10 mg/L thiamine HCl, 2.5 mg/L benzylaminopurine (BAP) and 20 nM DPP] contained in a 125 mL shake flask with a foam stopper. The flasks were placed on a rotary shaker at a speed of 125 rpm, in the dark, at a temperature of 28° C., for 7 days.

Transformation Experiment.

Transformation experiments were initiated by diluting BY2 suspension culture (grown as described above) with fresh medium to an $OD^{650}$ of 1.0. For each transformation target, 1.5 ml of diluted suspension was pipetted onto a sterile filter paper which had been placed on top of a vacuum filtration apparatus. Suspension cells were deposited evenly across the surface of the filter paper. The filter paper and cells were transferred to Bombardment Media [MS basal salts, 135 vitamins, 18.2 g/l mannitol, 18.2 g/L sorbitol, 30 g/L sucrose, 1 mg/L BAP, 0.1 mg/L 1-napthaleneacetic acid (NAA), 8 g/L TC Agar (PhytoTechnology Laboratories, A 175).

Plasmid Construct for Single Cell Plastid Transformation.

The DNA construct used in this example was designated pDAB3969. Construct elements were flanked by 16S trnI and trnA sequences from the tobacco chloroplast genome. Two genes, aphA-6 and nptII were used as selectable markers driven by the Prrn plus T7 gene 10 and PpsbA promoters, respectively. T7 gene 10 also drives the gene of interest, TurboGFP.

Biolistic Bombardment of BY2 Single Cells.

Cells remained on bombardment media for 4 hours prior to bombardment. Prepared targets were bombarded using a Bio-Rad PDS-1000/He Delivery System. Gold particles (0.4 µm, Inbio Gold Melbourne, Australia) were prepared, and DNA was precipitated on their surface using standard methods.

Target plates were bombarded at 1100 psi, together with 28 inches mercury vacuum, and 9 cm distance from stopping screen. Plates were then set aside for a single day recovery period. Filter papers plus tissue were then transferred to Medium C [LS salts, 120 g/L sucrose, 170 mg/L Potassium Phosphate, monobasic, anhydrous, 0.6 mg/L Thiamine-HCl, 0.2 mg/L 2,4-D, 8 g/L TC agar and 100 mg/L Kanamycin] and left on the original selection plate until resistant colonies appeared. When resistant colonies grew to be 4-5 mm in diameter, they were isolated onto individual plates with gel Media C and bulked up until they were large enough to be sampled for PCR analysis.

Results and Discussion.

BY2 suspension lines were cultured in Media A and Media B for 7 days. Five target plates were prepared from cells grown in Media A and five additional plates were prepared from cells grown in Media B. These two medias were designed to produce enlarged amyloplasts by boosting sucrose content, removing the auxin 2,4-dichlorophenoxy-acetic acid (2,4-D), and, in Media B, by the addition of the cytokinin BAP (1, 2). The enlarged amyloplasts served as larger targets for biolistic transformation. Both media that contained 20 nM DPP produced single cells. The bombarded plates produced 3 Kanamycin resistant colonies from Medium A treated cells and 2 resistant colonies from Media B treated cells.

Samples from each colony were sampled for molecular analysis. The DNA was extracted using DNasey protocol and the aliquots were analyzed by PCR using the following primer sets.

| Primer Name | Primer Sequence | |
|---|---|---|
| MAS394 | TATGCTGCGTTCGGGAAGGATGAA | set 2 |
| MAS395 | GATTAAAAGAATAAACATCCGATG | |
| MAS396 | TTGCCTAAGAGAGGATGCATCGGA | set 3 |
| MAS397 | TTGTCTGTTGTGCCCAGTCATAGC | |
| MAS398 | | set 4 |
| MAS399 | | |
| MAS400 | TGGAGTACCAGCACGCCTTCAAGC | set 5 |
| MAS401 | GGCTATGCCATCCTAAGGTGCTGC | |

Primers amplified segments of the transformation construct. Primer MAS401 lands in the native tobacco plastid DNA 83 base pairs beyond the end of the trnA flank and demonstrates integration into the plastid genome.

PCR reactions for primer sets 2, 3, 4, and 5 produced positive reactions for all five samples. DNA from wild type (non transformed) BY2 suspension cell or the tobacco plant control did not produce any bands. Thus the PCR results indicate the presence of all three transgenes and integration into the plastid genome.

The invention claimed is:

1. A method for producing a single plant cell, wherein said method comprises culturing plant cells comprising intact cell walls in medium containing glycerol and a separating agent selected from the group consisting of a pectin-degrading enzyme and a tubulin de-polymerizing compound, wherein said tubulin de-polymerizing compound conforms to the following formula:

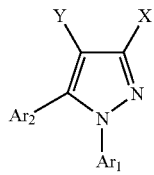

wherein
X=, OCH$_2$CO$_2$R,
Y=Cl,
Ar$_1$=unsubstituted phenyl,
Ar$_2$=unsubstituted phenyl; and
R=2carbon linear.

2. The method of claim 1, wherein said tubulin de-polymerizing compound is 4-chloro-1,5-diphenyl-1H-pyrazol-3-yloxy)-acetic acid ethyl ester.

3. The method of claim 1, wherein said tubulin de-polymerizing compound is

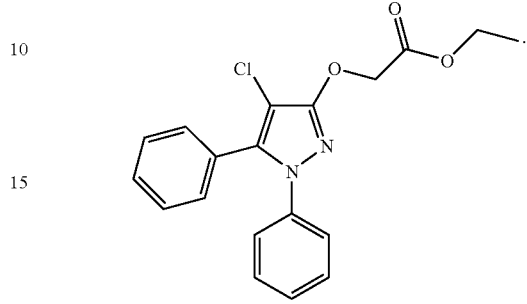

* * * * *